United States Patent
Bettati et al.

(10) Patent No.: US 7,271,191 B2
(45) Date of Patent: Sep. 18, 2007

(54) PYRAZOLE DERIVATIVES AS GAMMA-SECRETASE INHIBITORS USEFUL IN THE TREATMENT OF ALZHEIMER'S DISEASE

(75) Inventors: Michela Bettati, Sawbridgeworth (GB); Mark Stuart Chambers, Puckeridge (GB); Peter Alan Hunt, Saffron Walden (GB); Philip Jones, Pomezia (IT); Angus Murray MacLeod, Bishops Stortford (GB); Helen Jane Szekeres, Bisley (GB); Martin Richard Teall, Bishop Stortford (GB)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 0 days.

(21) Appl. No.: 10/549,226

(22) PCT Filed: Apr. 1, 2004

(86) PCT No.: PCT/GB2004/001452

§ 371 (c)(1),
(2), (4) Date: Sep. 9, 2005

(87) PCT Pub. No.: WO2004/089911

PCT Pub. Date: Oct. 21, 2004

(65) Prior Publication Data

US 2006/0264474 A1    Nov. 23, 2006

(30) Foreign Application Priority Data

Apr. 10, 2004 (GB) ................. 0308318.5

(51) Int. Cl.
*A61K 31/415* (2006.01)
*C07D 231/24* (2006.01)
*C07D 231/12* (2006.01)

(52) U.S. Cl. .............. 514/407; 514/406; 548/370.1; 548/371.7; 548/375.1

(58) Field of Classification Search .......... 548/370.1, 548/371.7, 375.1; 514/406, 407
See application file for complete search history.

(56) References Cited

FOREIGN PATENT DOCUMENTS

| EP | 1 104 759 | 6/2001 |
|---|---|---|
| WO | WO 00/66562 | 11/2000 |
| WO | WO 02/081433 | 10/2002 |
| WO | WO 03/093252 | 11/2003 |
| WO | WO 2004/031138 | 4/2004 |
| WO | WO 2004/039370 | 5/2004 |

OTHER PUBLICATIONS

Holsher, "Development of beta-amyloid, etc.," Reviews in the Neurosciences (2005), 16(3), 181-212.*
Behr et al., "Protease Inhibitors, etc.," Expert Opin. Investig. Drugs (2005), 14(11), 1385-1409.*
Dewachter et al., "Secretases as targets, etc.," The Lancet Neurology, 1, 2002, 409-416.*
Larner, "Secretases as therapeutic, etc.," Expert Opin. Ther. Patents (2004) 14(10), 1403-1420.*

* cited by examiner

*Primary Examiner*—Patricia L. Morris
(74) *Attorney, Agent, or Firm*—John C. Todaro; William Krovatin

(57) ABSTRACT

The compounds of formula I:

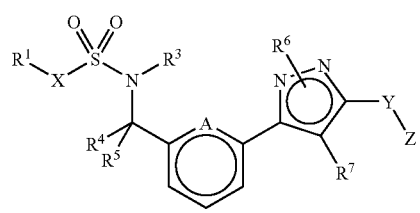

inhibit gamma secretase and hence are of utility in the treatment or prevention of Alzheimer's Disease.

8 Claims, No Drawings

PYRAZOLE DERIVATIVES AS GAMMA-SECRETASE INHIBITORS USEFUL IN THE TREATMENT OF ALZHEIMER'S DISEASE

CROSS REFERENCE TO RELATED APPLICATIONS

This application is a U.S. National Phase application under 35 U.S.C. § 371 of PCT Application No. PCT/GB2004/001452, filed Apr. 1, 2004, which claims priority under 35 U.S.C. § 119 from GB Application No. 0308318.5, filed Apr. 10, 2003.

The present invention relates to a novel class of compounds, their salts, pharmaceutical compositions comprising them, processes for making them and their use in therapy of the human body. In particular, the invention relates to novel sulphonamide, sulphamate and sulphamide derivatives, comprising a m-disubstituted benzene or pyridine ring and a substituted pyrazole moiety, which inhibit the processing of APP by γ-secretase, and hence are useful in the treatment or prevention of Alzheimer's disease.

Alzheimer's disease (AD) is the most prevalent form of dementia Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are relatively few reports in the literature of compounds with inhibitory activity towards γ-secretase, as measured in cell-based assays. These are reviewed in WO 01/70677. Many of the relevant compounds are peptides or peptide derivatives.

WO 01/70677 and WO 02/36555 disclose, respectively, sulphonamido- and sulphamido-substituted bridged bicycloalkyl derivatives which are believed to be useful in the treatment of Alzheimer's disease, but do not disclose or suggest compounds in accordance with the present invention.

The present invention provides a novel class of sulphonamide, sulphamate and sulphamide derivatives comprising a m-disubstituted benzene or pyridine ring. The compounds inhibit the processing of APP by the putative γ-secretase, and thus are useful in the treatment or prevention of AD.

According to the invention there is provided a compound of formula I:

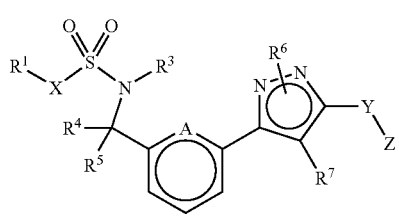

(I)

wherein:

A represents CH or N;

X represents a bond, O or $NR^2$;

Y represents a bond, $(CHR^8)_n$, $CR^8=CR^8$, $O-CHR^8$, $CHR^8-O$ or $CHR^8-NR^8$, where n is 1 or 2 and each $R^8$ is independently H or $C_{1-4}$alkyl;

Z represents Ar or $N(R^9)_2$, with the proviso that when Z represents $N(R^9)_2$, Y represents a bond or $(CHR^8)_n$;

$R^1$ represents a hydrocarbon group of 1-10 carbon atoms which is optionally substituted with up to 3 halogen atoms, or heteroaryl of 5 or 6 ring atoms optionally bearing up to 3 substituents independently selected from halogen, $CF_3$, $CHF_2$, $CH_2F$, $NO_2$, $CN$, $OCF_3$, $C_{1-6}$alkyl and $C_{1-6}$alkoxy; or when X represents $NR^2$, $R^1$ and $R^2$ together may complete a heterocyclic ring of up to 6 members which optionally bears up to 3 substituents independently selected from halogen, $CF_3$, $CHF_2$, $CH_2F$, $NO_2$, $CN$, $OCF_3$, $C_{1-6}$alkyl and $C_{1-6}$alkoxy, $R^2$ represents H or $C_{1-4}$alkyl, or together with $R^1$ completes a heterocyclic ring as defined above;

$R^3$ represents H or $C_{1-4}$alkyl;

$R^4$ represents $C_{1-6}$alkyl, $R^5$ represents H or $C_{1-6}$alkyl;

$R^6$ is bonded to one of the nitrogen atoms of the pyrazole ring and represents a hydrocarbon group of 1-5 carbon atoms which is optionally substituted with up to 3 halogen atoms;

$R^7$ represents H or $C_{1-6}$alkyl;

$R^9$ represents H or a hydrocarbon group of 1-10 carbon atoms which is optionally substituted with up to 3 halogen atoms, provided that at least one $R^9$ is not H; or the two $R^9$ groups complete a heterocyclic ring of 5 or 6 members which is optionally substituted with $CF_3$ or up to 3 halogen atoms; and Ar represents phenyl or 6-membered heteroaryl, either of which bears 0-3 substituents independently selected from halogen, $CF_3$, $CHF_2$, $CH_2F$, $NO_2$, $CN$, $OCF_3$, $C_{1-6}$alkyl and $C_{1-6}$alkoxy;

or a pharmaceutically acceptable salt thereof.

Where a variable occurs more than once in formula I or in a substituent thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The expression "$C_{3-6}$cycloalkyl" as used herein refers to nonaromatic monocyclic hydrocarbon ring systems comprising from 3 to 6 ring atoms. Examples include cyclopropyl, cyclobutyl, cyclopentyl, cyclohexyl and cyclohexenyl.

The expression "cycloalkylalkyl" as used herein includes groups such as cyclopropylmethyl, cyclobutylmethyl, cyclopentylmethyl and cyclohexylmethyl.

The term "halogen" as used herein includes fluorine, chlorine, bromine and iodine, of which fluorine and chlorine are preferred.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, A represents CH or N, and thus completes a benzene or pyridine ring. Preferably, A represents CH.

In the compounds of formula I, X represents a bond, O or $NR^2$, but preferably represents a bond or $NR^2$.

Y represents a bond or a linking group selected from $(CHR^8)_n$, $CR^8=CR^8$, $O-CHR^8$, $CHR^8-O$ or $CHR^8-NR^8$, where n is 1 or 2 and each $R^8$ is independently H or $C_{1-4}$alkyl. Suitable identities for $R^8$ include H, methyl and ethyl, but preferably Y comprises at most one $R^8$ group that is other than H. Suitable identities for Y include a bond, $CH_2$, $CH_2CH_2$, $CH=CH$, $OCH_2$, $CH_2O$, $CH(Me)O$, $CH_2NH$ and $CH_2N(Et)$. When Z is Ar, preferred identities for Y include $CH_2$, $OCH_2$, $CH_2CH_2$ and $CH_2O$, especially $CH_2O$. When Z is $N(R^9)_2$, Y is preferably $CH_2$.

Suitable hydrocarbon groups represented by $R^1$ include alkyl, cycloalkyl, cycloalkylalkyl, alkenyl, phenyl and benzyl groups optionally bearing up to 3 halogen substituents, the preferred halogen substituent being fluorine or chlorine, especially fluorine. Said alkyl, cycloalkyl, cycloalkylalkyl and alkenyl groups typically comprise up to 6 carbon atoms. Examples of hydrocarbon and fluorinated hydrocarbon groups represented by $R^1$ include 4-fluorophenyl, benzyl, n-propyl, 2,2-dimethylpropyl, n-butyl, isopropyl, t-butyl, 2,2,2-trifluoroethyl, 3,3,3-trifluoropropyl, allyl, cyclobutyl and cyclopropylmethyl.

Heteroaryl groups represented by $R^1$ are either 5-membered or 6-membered and are optionally substituted as defined previously. Preferred 5-membered heteroaryl groups include those containing a sulphur atom, such as thienyl, thiazolyl and isothiazolyl. Preferred 6-membered heteroaryl groups include pyridyl, in particular 3-pyridyl. Preferred substituents include halogen (especially chlorine or fluorine), $CF_3$ and alkyl (such as methyl). If two or more substituents are present, preferably not more than one of them is other than halogen or alkyl. Preferred heteroaryl groups are unsubstituted or monosubstituted with halogen.

When $R^1$ represents an optionally substituted phenyl, benzyl or heteroaryl group, X is preferably a bond.

When X represents $NR^2$, $R^1$ may combine with $R^2$ to complete a heterocyclic ring of up to 6 members which is optionally substituted as defined previously. Said ring preferably comprises at most one heteroatom selected from O, N and S in addition to the nitrogen to which $R^1$ and $R^2$ are mutually attached. Suitable rings include azetidinyl, pyrrolidinyl, piperidinyl, piperazinyl, morpholinyl and thiomorpholinyl. Preferred substituents include $CF_3$, halogen (especially chlorine or fluorine) and alkyl such as methyl. If two or more substituents are present, preferably not more than one of them is other than halogen or alkyl.

$R^2$ may alternatively represent H or $C_{1-4}$alkyl, such as methyl.

Preferably, $R^2$ represents H.

$R^3$ represents H or $C_{1-4}$alkyl, such as methyl, but preferably represents H.

$R^4$ represents $C_{1-6}$alkyl, preferably $C_{1-4}$alkyl, and $R^5$ represents H or $C_{1-6}$alkyl, preferably H or $C_{1-4}$alkyl. Suitable alkyl groups include methyl and ethyl. Preferably, $R^4$ is methyl and $R^5$ is H, or both of $R^4$ and $R^5$ are methyl. Most preferably, both of $R^4$ and $R^5$ represent methyl.

$R^6$ may be attached to either of the nitrogen atoms in the pyrazole ring. In one embodiment, $R^6$ is attached to the nitrogen atom that is adjacent to the carbon atom to which Y is attached. In an alternative (preferred) embodiment, $R^6$ is attached to the nitrogen atom which is remote from the carbon atom to which Y is attached. $R^6$ represents a hydrocarbon group of 1-5 carbon atoms which is optionally substituted with up to 3 halogen atoms, and thus may comprise cyclic or acyclic hydrocarbon residues or combinations thereof, saturated or unsaturated, up to a maximum of 5 carbon atoms in total. The hydrocarbon group represented by $R^6$ is preferably unsubstituted or is substituted with up to 3 fluorine atoms Examples include methyl, ethyl, n-propyl, isopropyl, n-butyl, sec-butyl, t-butyl, fluoromethyl, difluoromethyl, trifluoromethyl, 2,2,2-trifluoroethyl, cyclopropyl, cyclopropylmethyl and allyl. Preferred examples include methyl, ethyl and isopropyl, especially methyl and ethyl. Most preferably, $R^6$ represents ethyl.

$R^7$ represents H or $C_{1-6}$alkyl, preferably H or $C_{1-4}$alkyl such as methyl or ethyl. Most preferably, $R^7$ represents H.

$R^9$ represents H or a hydrocarbon group as defined previously, or the two $R^9$ groups complete a heterocyclic ring as defined previously. The two $R^9$ groups cannot both be H. Preferred hydrocarbon groups are $C_{1-6}$alkyl, optionally bearing up to 3 halogen substituents, fluorine being preferred. Suitable examples include 3,3,3-trifluoropropyl. Preferably, the two $R^9$ groups complete a 5- or 6- (preferably 6-) membered ring, optionally substituted with up to 3 halogens or with $CF_3$. Said ring preferably comprises not more than one heteroatom, selected from N, O and S, in addition to the N atom to which the $R^9$ groups are attached. Preferred rings include piperidine, morpholine and tetrahydropyridine. Suitable identities for the $N(R^9)_2$ moiety include 3,3,3-trifluoropropylamino, 4,4-difluoropiperidin-1-yl, morpholin-4-yl, 4-(trifluoromethyl)piperidine-1-yl, and 4-trifluoromethyl-1,2,3,6-tetrahydropyridin-1-yl, of which 4-trifluoromethyl-1,2,3,6-tetrahydropyridin-1-yl is particularly preferred.

Ar represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy. Examples of suitable 6-membered heteroaryl groups represented by Ar include pyridyl, pyrazinyl, pyrimidinyl, pyridazinyl and triazinyl, of which pyridyl is a preferred example. Preferably, the phenyl or heteroaryl ring bears 0 to 2 substituents. Preferred substituents include halogen (especially chlorine and fluorine), CN, $C_{1-6}$alkyl (especially methyl), $C_{1-6}$alkoxy (especially methoxy), $OCF_3$ and $CF_3$. If two or more substituents are present, preferably not more than one of them is other than halogen or alkyl. Examples of groups represented by Ar include phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Suitable specific values for Ar include phenyl, 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 3,4,5-trifluorophenyl, 2-cyanophenyl, 3-cyanophenyl, 4-cyanophenyl, 4-methylphenyl, 3-methoxyphenyl, 4-methoxyphenyl, 2-(trifluoromethyl)phenyl, 4-(trifluoromethyl)phenyl, 4-(trifluoromethoxy)phenyl, pyridin-2-yl, pyridin-3-yl, pyridin-4-yl, pyrazin-2-yl, 5-methylpyridin-2-yl, 5-fluoropyridin-2-yl, 5-chloropyridin-2-yl, 5-(trifluoromethyl)pyridin-2-yl and 6-(trifluoromethyl)pyridin-3-yl. Preferred examples include phenyl, 4-fluorophenyl, 2-fluorophenyl, 3-fluorophenyl, 4-cyanophenyl, 3-cyanophenyl, 2-cyanophenyl, 2-chlorophenyl and 3-methoxyphenyl.

In a particularly preferred embodiment, Ar represents 4-fluorophenyl.

In one subset of the compounds of formula I, X is a bond and $R^1$ represents $C_{1-6}$alkyl which is optionally substituted with up to 3 fluorine atoms, or phenyl, benzyl or 5- or 6-membered heteroaryl, any of which is optionally substituted with chlorine or fluorine. Within this embodiment, suitable identities for $R^1$ include n-propyl, n-butyl, 2,2,2-trifluoroethyl, benzyl, 4-fluorophenyl, 2-thienyl, 5-chloro-2-thienyl, 5-isothiazolyl and 6-chloro-pyridin-3-yl. Within this embodiment, preferred identities for $R^1$ include n-propyl, 2,2,2-trifluoroethyl, 4-fluorophenyl, benzyl, 2-thienyl and 5-chloro-2-thienyl, in particular 2,2,2-trifluoroethyl and 5-chloro-2-thienyl.

In a second subset of the compounds of formula I, X is O and $R^1$ represents alkyl, alkenyl, cycloalkyl or cycloalkylalkyl of up to 6 carbon atoms which is optionally substituted with up to 3 fluorine atoms.

In a third subset of the compounds of formula I, X is NH or NMe and $R^1$ represents alkyl, alkenyl, cycloalkyl or cycloalkylalkyl of up to 6 carbon atoms which is optionally substituted with up to 3 fluorine atoms. Within this embodiment, suitable identities for $R^1$ include ethyl, n-propyl, isopropyl, n-butyl, 2,2-dimethylpropyl, t-butyl, 2,2,2-trifluoroethyl, 3,3,3-trifluoropropyl, cyclobutyl, cyclopentyl and cyclopropylmethyl.

In a fourth subset of the compounds of formula I, X represents $NR^2$ and $R^1$ and $R^2$ complete a heterocyclic ring as described previously.

In a fifth subset of the compounds of Formula I, Z represents Ar.

Specific compounds in accordance with the invention are disclosed in the Examples appended hereto.

The compounds of the present invention have an activity as inhibitors of γ-secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and poly(ethylene glycol), and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's disease, a suitable dosage level is about 0.01 to 250 mg/kg per day, preferably about 0.05 to 100 mg/kg per day, more preferably about 0.1 to 50 mg/kg of body weight per day, and for the most preferred compounds, about 0.1 to 10 mg/kg of body weight per day. The compounds may be administered on a regimen of 1 to 4 times per day. In some cases, however, a dosage outside these limits may be used.

The compounds of formula I may be prepared by reaction of an amine (1) with $R^1$—X—$SO_2Cl$:

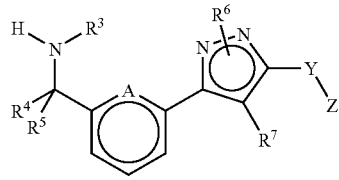
(1)

where A, X, Y, $R^1$, $R^3$, $R^4$, $R^5$, $R^6$, $R^7$ and Z have the same meanings as before. The reaction typically takes place at ambient temperature in an aprotic solvent such as dichloromethane in the presence of a base such as triethylamine.

Amines (1) in which $R^3$ is H and $R^5$ is H may be prepared by reaction of nitriles (2) with $R^4$Mg-Hal and $LiAlH_4$:

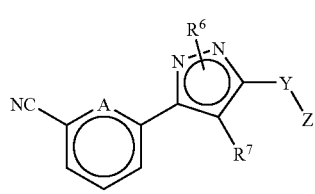
(2)

where Hal represents halogen (especially bromine or iodine) and A, Y, $R^4$, $R^6$, $R^7$ and Z have the same meanings as before. The reaction may be carried out in THF at ambient temperature.

Amines (1) in which $R^3$ is H and $R^4$ and $R^5$ represent identical alkyl groups may be prepared by treatment of nitriles (2) with excess $R^4$Li in the presence of $CeCl_3$. The reaction takes place between −78° C. and ambient temperature in THF.

Amines (1) in which $R^3$ is alkyl may be prepared by N-alkylation of the corresponding primary amines using standard techniques.

Nitriles (2) may be prepared by reaction of keto-enols (3) with $R^6NHNH_2$:

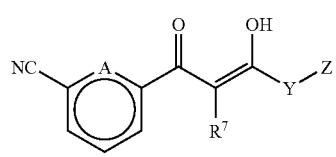
(3)

where A, Y, $R^6$, $R^7$ and Z have the same meanings as before. The reaction may be carried out in refluxing ethanol and typically provides a mixture of both the positional isomers, which is separable by chromatography.

Keto-enols (3) in which $R^7$ is H may be obtained by reaction of ketones (4) with Z-Y—$CO_2R$:

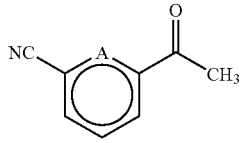
(4)

where R is H or $C_{1-4}$alkyl such as methyl, and A, Y and Z have the same meanings as before. The reaction takes place in the presence of lithium diisopropylamide in THF between −78° C. and ambient temperature. When a carboxylic acid Z-Y—$CO_2H$ is used as the reagent, it is preferably prereacted with 1,1′-carbonyldiimidazole.

Keto-enols (3) in which $R^7$ is alkyl may be obtained by alkylation of the corresponding keto-enols in which $R^7$ is H, e.g. by refluxing with the appropriate alkyl iodide in acetone in the presence of alkali metal carbonate.

An alternative route to nitriles (2) in which $R^7$ is H involves reaction of triflates (5) with 3-cyanobenzeneboronic acid or 6-cyanopyridine-2-boronic acid as appropriate:

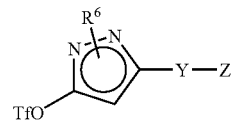
(5)

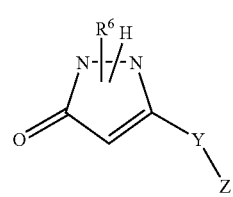
(6)

where Tf represents trifluoromethanesulphonyl(triflyl) and $R^6$, Y and Z have the same meanings as before. Very aptly, Y is a bond and Z is Ar. The reaction may be carried out in refluxing toluene in the presence of a base such as sodium carbonate and a palladium catalyst such as $(Ph_3P)_4Pd(0)$. Triflates (5) are available by treatment of pyrazolones (6) with triflic anhydride in pyridine, e.g. at −10° C. to ambient temperature. Pyrazolones (6) in which Y is a bond and Z is Ar are obtainable by reaction of $R^6NHNH_2$ with Ar—C≡C—$CO_2Me$, where $R^6$ and Ar have the same meanings as before. The reaction may be carried out in refluxing methanol, and typically provides a mixture of the two positional isomers which may be separated by conventional means.

An alternative route to nitrites (2) in which Y represents $CHR^8$—O involves reaction of Ar—OH with alcohols (7):

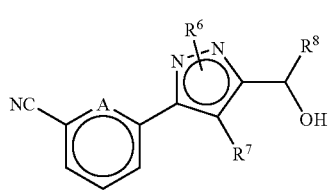
(7)

-continued

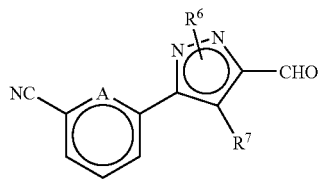
(8)

where A, $R^6$, $R^7$, $R^8$ and Ar have the same meanings as before. The reaction may be carried out in THF at ambient temperature in the presence of triphenylphosphine and a dialkylazodicarboxylate. Alcohols (7) are available by treatment of the corresponding aldehydes (8) with sodium borohydride (when $R^8$ is H) or with the appropriate Grignard reagent (when $R^8$ is alkyl). The aldehydes (8) are obtainable by acid hydrolysis of acetals (9):

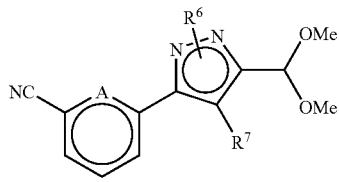
(9)

where A, $R^6$, $R^7$, $R^8$ and Ar have the same meanings as before. The acetals (9) are obtained by condensation of methylglyoxal dimethylacetal with 3-cyanobenzoyl chloride or 6-cyanopyrid-2-oyl chloride as appropriate, followed by optional alkylation of the resulting keto-enol and treatment thereof with $R^6NHNH_2$ in the manner described above for the conversion of (3) to (2). The condensation of methylglyoxal dimethylacetal with 3-cyanobenzoyl chloride or 6-cyanopyrid-2-oyl chloride may be carried out in THF at −78° C. in the presence of lithium diisopropylamide.

An alternative route to nitriles (2) in which Y represents $CH_2$—$NR^8$ involves reaction of aldehydes (8) with $ArNHR^8$ and sodium cyanoborohydride, where $R^8$ and Ar have the same meanings as before. Alternatively, the alcohol group in (7) may be converted to a leaving group such as chloride, mesylate or tosylate, then reacted with $ArNHR^8$. Similarly, displacement of said leaving group by reaction with $(R^9)_2$NH provides nitriles (2) in which Y is $CH_2$ and Z is $N(R^9)_2$.

It will be apparent to those skilled in the art that the reaction steps summarised above need not always be carried out in the sequence described above. For example, the nitrile group in compounds (9) may be subjected to reductive alkylation as described for the conversion of (2) to (1), and the resulting amine reacted with $R^1$—X—$SO_2Cl$, prior to the elaboration of the acetal group into the Y-Z moiety.

It will also be appreciated that a given compound in accordance with formula I may be converted into another compound also in accordance with formula I by means of standard synthetic techniques such as alkylation, oxidation, reduction, esterification, amide coupling, hydrolysis, electrophilic substitution and nucleophilic substitution. Alternatively, such conversions may be carried out on synthetic precursors of the compounds of formula I.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

Where they are not commercially available, the starting materials and reagents used in the above-described synthetic schemes may be prepared by conventional means.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, $3^{rd}$ Ed., John Wiley & Sons, 1999. The protecting groups may be removed at a convenient subsequent stage using methods known from the art.

An assay which can be used to determine the level of activity of compounds of the present invention is described in WO01/70677. A preferred assay to determine such activity is as follows:

1) SH-SY5Y cells stably overexpressing the βAPP C-terminal fragment SPA4CT are cultured at 50-70% confluency. 10 mM sodium butyrate is added 4 hours prior to plating.
2) Cells are plated in 96-well plates at 35,000 cells/well/100 μL in Dulbeccos minimal essential medium (DMEM) (phenol red-free)+10% foetal bovine serum (FBS), 50 mM HEPES buffer (pH7.3), 1% glutamine.
3) Make dilutions of the compound plate. Dilute stock solution 18.2× to 5.5% DMSO and 11× final compound concentration. Mix compounds vigorously and store at 4° C. until use.
4) Add 10 μL compound/well, gently mix and leave for 18 h at 37° C., 5% $CO_2$.
5) Prepare reagents necessary to determine amyloid peptide levels, for example by Homogeneous Time Resolved Fluorescence (HTRF) assay.
6) Plate 160 μL aliquots of HTRF reagent mixture to each well of a black 96-well HTRF plate.
7) Transfer 40 μL conditioned supernatant from cell plate to HTRF plate. Mix and store at 4° C. for 18 hours.
8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.
9) Add 10 μL/well MTS/PES solution to the cells; mix and leave at 37° C.
10) Read plate when the absorbance values are approximately 0.4-0.8. (Mix briefly before reading to disperse the reduced formazan product).

EXAMPLES

Example 1

2,2,2-Trifluoro-N-[1-(3-{3-[4-fluorophenoxymethyl]-1-methyl-1H-pyrazol-5-yl}phenyl)-1-methylethyl]ethanesulfonamide

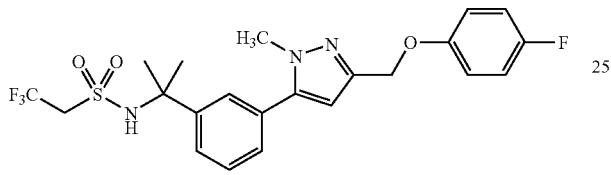

Step 1: 3-(5-Dimethoxymethyl-1-methyl-1H-pyrazol-3-yl)-benzonitrile and 3-(3-Dimethoxymethyl-1-methyl-1H-pyrazol-5-yl)-benzonitrile

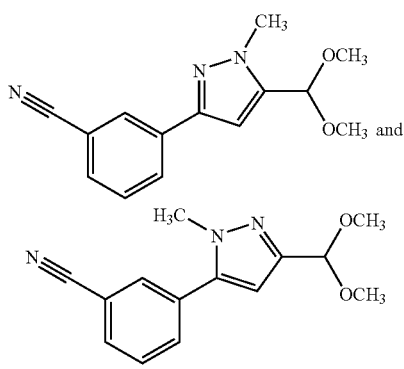

A solution of BuLi (66 mmol) in hexanes (1.6 M, 41.2 mL) was added dropwise over 10 min to a stirred solution of $^i$Pr$_2$NH (9.2 mL, 66 mmol) in THF (50 mL) at 0° C. under N$_2$. After 40 min. the reaction was cooled to −78° C. and a solution of methylglyoxal dimethyl acetal (7.81 mL, 66 mmol) in THF (40 mL) was added dropwise over 10 min and the mixture was stirred for a further hour. A solution of 3-cyanobenzoyl chloride (4.96 g, 30 mmol) in THF (30 mL) was added over 1 min and the reaction stirred at −78° C. for 30 min before warming to RT and stirring for a further hour. The reaction was quenched by the addition of 1M citric acid solution (100 mL) and then extracted with Et$_2$O (2×150 mL). The combined organic extracts were washed with brine (50 mL), dried (MgSO$_4$) and concentrated under reduced pressure to yield the crude 1,3-dicarbonyl compound.

MeOH (50 mL) and methylhydrazine (3.2 mL, 60 mmol) were added to this crude residue and the mixture heated at reflux for 90 min. The solvent was removed under reduced pressure and the residue purified by column chromatography on silica eluting with 50% EtOAc/iso-hexanes to yield first 3-(5-dimethoxymethyl-1-methyl-1H-pyrazol-3-yl)-benzonitrile (3.3 g, 42%) and then the eluent was changed to 100% EtOAc to yield 3-(3-dimethoxymethyl-1-methyl-1H-pyrazol-5-yl)-benzonitrile (2.5 g, 32%).

3-(5-Dimethoxymethyl-1-methyl-1H-pyrazol-3-yl)-benzonitrile: $^1$H NMR (CDCl$_3$, 500 MHz) δ 8.07 (1H, s), 7.99 (1H, d, J=7.9 Hz), 7.54 (1H, d, J=7.9 Hz), 7.47 (1H, t, J=7.9 Hz), 6.66 (1H, s), 5.50 (1H, s), 3.93 (3H, s), 3.36 (6H, s).

3-(3-Dimethoxymethyl-1-methyl-1H-pyrazol-5-yl)-benzonitrile: $^1$H NMR (CDCl$_3$, 500 MHz) δ 7.75-7.65 (3H, m), 7.60 (1H, t, J=7.7 Hz), 6.42 (1H, s), 5.49 (1H, s), 3.89 (3H, s), 3.44 (6H, s).

Step 2: 1-[3-(3-Dimethoxymethyl-1-methyl-1H-pyrazol-5-yl)-phenyl]-1-methylethylamine

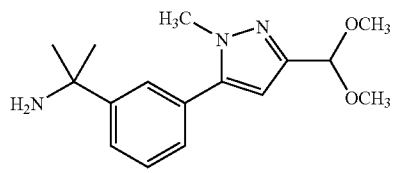

Anhydrous CeCl$_3$ (8.28 g, 33.6 mmol) was pulverised and dried at 140° C., 1 mm Hg for 1 hour. After cooling to RT and introducing a N$_2$ atmosphere, THF (200 mL) was added and the suspension was stirred for 15 min. The white slurry was cooled to −78° C. and a solution of MeLi (33.6 mmol) in Et$_2$O (1.6 M, 21.0 mL) added dropwise over 5 min. After a further hour, a solution of 3-(3-dimethoxymethyl-1-methyl-1H-pyrazol-5-yl)-benzonitrile (1.0 g, 3.89 mmol) in THF (10 mL) was added and the reaction stirred overnight gradually warming to RT. The reaction was quenched by the cautious addition of NH$_4$Cl solution (100 mL) and then the organics were extracted with EtOAc (3×100 mL). The combined organics were washed with brine (100 mL), dried (MgSO$_4$) and concentrated under reduced pressure. The mixture was then purified by column chromatography on deactivated alumina eluting with 2% MeOH/CH$_2$Cl$_2$ to yield the amine (267 mg, 24%). $^1$H NMR (CDCl$_3$, 500 MHz) δ 7.57-7.50 (2H, m), 7.41 (1H, t, J=7.8 Hz), 7.26 (1H, d, J=7.8 Hz), 6.38 (1H, s), 5.50 (1H, s), 3.88 (3H, s), 3.44 (6H, s), 1.52 (6H, s).

Step 3: 2,2,2-Trifluoroethanesulfonic acid {1-[3-(3-dimethoxymethyl-1-methyl-1H-pyrazol-5-yl)-phenyl]-1-methylethyl}-amide

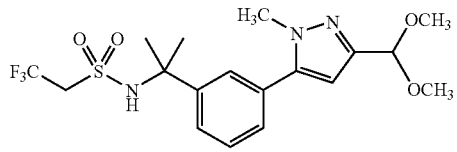

2,2,2-Trifluoroethylsulfonyl chloride (253 mg, 1.4 mmol) was added dropwise to a stirred solution of the amine from Step 2 (267 mg, 0.92 mmol) and Et$_3$N (193 μL, 1.4 mmol) in CH$_2$Cl$_2$ (25 mL) at RT under N$_2$. The mixture was stirred at RT for 30 min and then diluted with CH$_2$Cl$_2$ (25 mL), washed with NaHCO$_3$ solution (20 mL) and concentrated under reduced pressure to yield the crude sulfonamide (213 mg, 53%). $^1$H NMR (CDCl$_3$, 360 MHz) δ 7.60-7.53 (2H, m), 7.49 (1H, t, J=7.6 Hz), 7.37 (1H, d, J=7.6 Hz), 6.38 (1H, s), 5.50 (1H, s), 5.02 (1H, s), 3.88 (3H, s), 3.47 (2H, q, J=8.8 Hz), 3.44 (6H, s), 1.81 (6H, s). MS (ES$^+$) C$_{18}$H$_{24}$F$_3$N$_3$O$_4$S requires: 435, found: 404 (M-OCH$_3$$^+$, 100%).

Step 4: 2,2,2-Trifluoroethanesulfonic acid {1-[3-(3-formyl-1-methyl-1H-pyrazol-5-yl)-phenyl]-1-methylethyl}-amide

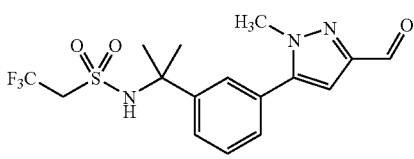

The sulfonamide from Step 3 (209 mg, 0.48 mmol), TFA (0.5 mL), H$_2$O (2.0 mL) and THF (5.0 mL) were stirred together at RT for 2 hours and then concentrated under reduced pressure to remove the organic solvents. The residue was neutralised with NaHCO$_3$ solution (20 mL), extracted with EtOAc (2×30 mL), dried (MgSO$_4$) and concentrated under reduced pressure to yield the crude aldehyde (170 mg, 91%). $^1$H NMR (CDCl$_3$, 400 MHz) δ 9.88 (1H, s), 7.55-7.47 (2H, s), 7.44 (1H, t, J=7.5 Hz), 7.29 (1H, d, J=7.5 Hz), 6.77 (1H, s), 5.44 (1H, s), 3.90 (3H, s), 3.46 (2H, q, J=8.9 Hz), 1.74 (6H, s). MS (ES$^+$) C$_{16}$H$_{18}$F$_3$N$_3$O$_3$S requires: 389, found: 390 (M+H$^+$, 100%).

Step 5: 2,2,2-Trifluoroethanesulfonic acid {1-[3-(3-hydroxymethyl-1-methyl-1H-pyrazol-5-yl)-phenyl]-1-methylethyl}-amide

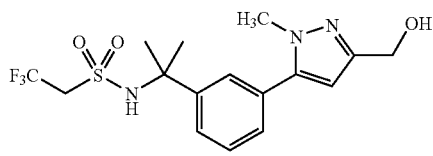

NaBH$_4$ (8.2 mg, 0.22 mmol) was added to a stirred solution of the aldehyde from Step 4 (85 mg, 0.22 mmol) in EtOH (5 mL) at RT and the mixture was stirred for a further 30 min. NH$_4$Cl solution (5 ml) was added and the EtOH removed under reduced pressure. The aqueous residue was extracted with EtOAc (2×30 mL), and the organics dried and concentrated under reduced pressure to yield the crude alcohol (75 mg, 88%). $^1$H NMR (CDCl$_3$, 360 MHz) δ 7.55-7.48 (2H, s), 7.42 (1H, t, J=7.5 Hz), 7.29 (1H, d, J=7.5 Hz), 6.25 (1H, s), 5.00 (1H, s), 4.64 (2H, s), 3.78 (3H, s), 3.41 (2H, q, J=8.9 Hz), 1.75 (6H, s). MS (ES$^+$) C$_{16}$H$_{20}$F$_3$N$_3$O$_3$S requires: 391, found: 392 (M+H$^+$, 100%).

Step 6: 2,2,2-Trifluoro-N-[1-(3-{3-[4-fluorophenoxymethyl]-1-methyl-1H-pyrazol-5-yl}phenyl)-1-methylethyl]ethanesulfonamide

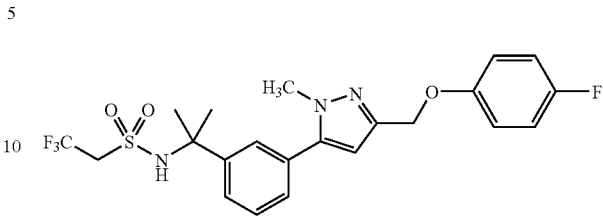

Diisopropyl azodicarboxylate (57 mg, 0.27 mmol) was added dropwise to a stirred solution of the alcohol from Step 5 (75 mg, 0.19 mmol), PPh$_3$ (75 mg, 0.27 mmol) and 4-fluorophenol (26 mg, 0.23 mmol) in THF (10 mL) under N$_2$ and the resulting mixture was stirred at RT for 2 hours. Further DIAD (19 mg, 0.09 mmol), PPh$_3$ (25 mg, 0.09 mmol) and 4-fluorophenol (11 mg, 0.09 mmol) were added and stirring was continued for a further 30 min. The reaction mixture was then concentrated under reduced pressure while loading on to MgSO$_4$ and then purified by column chromatography on silica eluting with 100% Et$_2$O to yield the desired ether (19 mg, 20%). $^1$H NMR (CDCl$_3$, 360 MHz) δ 7.58-7.53 (2H, s), 7.49 (1H, t, J=7.5 Hz), 7.37 (1H, d, J=7.5 Hz), 6.97 (4H, app. d, J=6.1 Hz), 6.41 (1H, s), 5.05 (2H, s), 4.99 (1H, s), 3.88 (3H, s), 3.48 (2H, q, J=8.9 Hz), 1.81 (6H, s). MS (ES$^+$) C$_{22}$H$_{23}$F$_4$N$_3$O$_3$S requires: 485, found: 486 (M+H$^+$, 100%).

Example 2

N-Cyclobutyl-N'-[1-(3-{1-ethyl-3-[(4-fluorophenoxy)methyl]-1H-pyrazol-5-yl}phenyl)-1-methylethyl]sulfamide

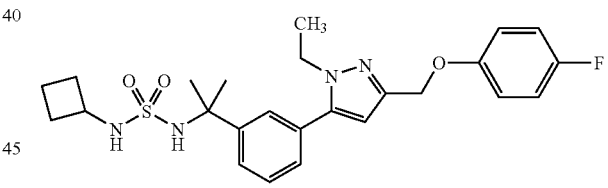

Step 1: 3-(3-Dimethoxymethyl-1-ethyl-1H-pyrazol-5-yl)-benzonitrile

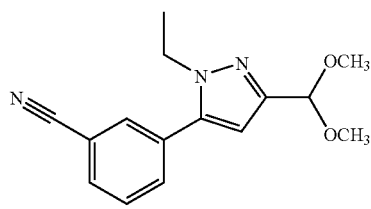

Prepared as described in Example 1 Step 1, substituting ethylhydrazine oxalate for methylhydrazine. The product was purified by column chromatography on silica eluting with 50-100% EtOAc/iso-hexanes to separate it from the 1-ethyl-1H-pyrazol-3-yl isomer.

$^1$H NMR (CDCl$_3$, 500 MHz) δ 7.78-7.55 (4H, m), 6.38 (1H, s), 5.49 (1H, s), 4.15 (2H, q, J=7.3 Hz), 3.44 (6H, s), 1.40 (3H, t, J=7.3 Hz).

Step 2: 3-(1-Ethyl-3-formyl-1H-Pyrazol-5-yl)-benzonitrile

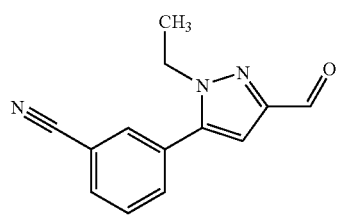

A mixture of 3-(3-dimethoxymethyl-1-ethyl-1H-pyrazol-5-yl)-benzonitrile (5.0 g, 18.4 mmol), TFA (5.0 mL), H$_2$O (20 mL) and THF (50 mL) was stirred at RT for 1 hour and then concentrated under reduced pressure to remove the organic solvents. The residue was neutralised with 1N NaOH solution (100 mL), extracted with EtOAc (2×150 mL), dried (MgSO$_4$) and concentrated under reduced pressure while dry loading onto MgSO$_4$. The mixture was then purified by column chromatography on silica eluting with 35-60% EtOAc/iso-hexanes to yield the desired aldehyde (2.91 g, 70%). $^1$H NMR (CDCl$_3$, 500 MHz) δ 10.00 (1H, s), 7.80-7.72 (1H, m), 7.70 (1H, s), 7.67-7.60 (2H, m), 6.84 (1H, s), 4.23 (2H, q, J=7.3 Hz), 1.49 (3H, t, J=7.3 Hz). MS (ES$^+$) C$_{13}$H$_{11}$N$_3$O requires: 225, found: 226 (M+H$^+$, 100%).

Step 3: 3-(1-Ethyl-3-hydroxymethyl-1H-pyrazol-5-yl)-benzonitrile

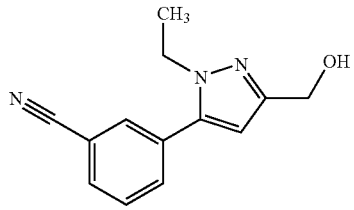

NaBH$_4$ (252 mg, 6.6 mmol) was added portionwise to a stirred solution of 3-(1-ethyl-3-formyl-1H-pyrazol-5-yl)-benzonitrile (1.5 g, 6.6 mmol) in EtOH (25 mL) at 0° C. The mixture was warmed to RT and stirred for a further 30 min., NH$_4$Cl solution (10 ml) was added, the EtOH removed under reduced pressure, H$_2$O (30 mL) added, and the aqueous mixture extracted with EtOAc (2×70 mL). The combined organic extracts were washed with brine (25 mL), dried (MgSO$_4$) and concentrated under reduced pressure to yield the crude alcohol (1.49 g, quant.). $^1$H NMR (CDCl$_3$, 360 MHz) δ 7.78-7.54 (4H, m), 6.31 (1H, s), 4.72 (2H, s), 4.11 (2H, q, J=7.3 Hz), 1.42 (3H, t, J=7.3 Hz). MS (ES$^+$) C$_{13}$H$_{13}$N$_3$O requires: 227, found: 228 (M+H$^+$, 70%).

Step 4: 3-[1-Ethyl-3-(4-fluorophenoxymethyl)-1H-pyrazol-5-yl]-benzonitrile

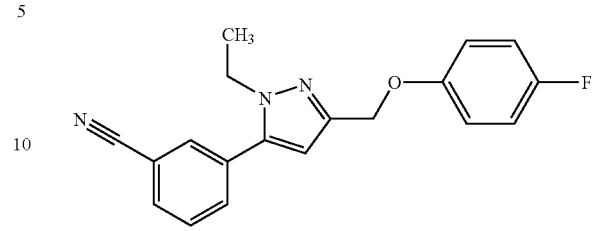

Prepared by the procedure of Example 1 Step 6, using 1.0 g, (4.4 mmol) of the alcohol obtained in Step 3 above. The product was purified twice by column chromatography on silica, eluting once with 30-45% EtOAc/iso-hexane and again using 25% Et$_2$O/toluene to yield the desired ether (702 mg, 50%). $^1$H NMR (CDCl$_3$, 360 MHz) δ 7.76-7.57 (4H, m), 7.03-6.90 (4H, m), 6.40 (1H, s), 5.06 (2H, s), 4.13 (2H, q, J=7.2 Hz), 1.43 (3H, t, J=7.2 Hz). MS (ES$^+$) C$_{19}$H$_{16}$FN$_3$O requires: 321, found: 322 (M+H$^+$, 65%).

Step 5: 1-{3-[1-Ethyl-3-(4-fluoro-phenoxymethyl)-1H-pyrazol-5-yl]-phenyl}-1-methylethyl amine

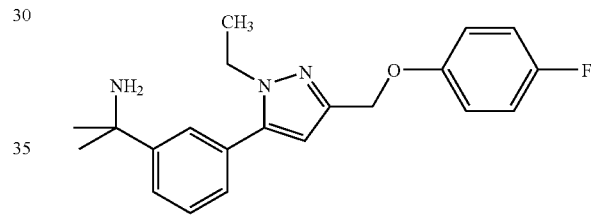

Prepared by the procedure of Example 1 Step 2 using the product of Step 4 (702 mg, 2.19 mmol), CeCl$_3$ (5.37 g, 21.9 mmol) and MeLi (1.6 M in Et$_2$O, 13.7 mL, 21.9 mmol) to yield, after purification by column chromatography on deactivated alumina using 1-4% MeOH/CH$_2$Cl$_2$, the amine (296 mg, 38%). $^1$H NMR (CDCl$_3$, 500 MHz) δ 7.63-7.56 (3H, m), 7.48 (1H, t, J=7.5 Hz), 6.98 (4H, app. d, J=6.3 Hz), 6.37 (1H, s), 5.06 (2H, s), 4.14 (2H, q, J=7.3 Hz), 1.52 (6H, s), 1.43 (3H, q, J=7.3 Hz). MS (ES$^+$) C$_{21}$H$_{24}$FN$_3$O requires: 353, found: 337 (M-OCH$_3$+H$^+$, 100%).

Step 6: N-Cyclobutyl-N'-[1-(3-{1-ethyl-3-[(4-fluorophenoxy)methyl]-1H-pyrazol-5-yl}phenyl)-1-methylethyl]sulfamide

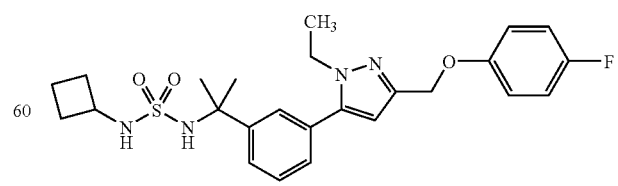

Prepared by the procedure of Example 1 Step 3 using the amine from Step 5 (100 mg, 0.28 mmol), Et$_3$N (114 mg, 1.1 mmol) and cyclobutylsulfamoyl chloride (192 mg, 1.1 mmol) to yield, after purification by column chromatography on silica using 70% Et$_2$O/iso-hexanes and then by normal phase preparative HPLC, the sulfamide (17.5 mg, 12%). $^1$H NMR (CDCl$_3$, 360 MHz) δ 7.60-7.52 (2H, m), 7.44 (1H, t, J=7.6 Hz), 7.30 (1H, d, J=7.6 Hz), 6.97 (4H, app. d, J=6.3 Hz), 6.37 (1H, s), 5.06 (2H, s), 4.55 (1H, s), 4.12 (2H, q, J=7.3 Hz), 3.78 (1H, app. sextet, J=8.3 Hz), 2.45-2.35 (2H, m), 1.93-1.82 (2H, m), 1.75 (6H, s), 1.72-1.60 (2H, m), 1.44 (3H, J=7.3 Hz). MS (ES$^+$) C$_{25}$H$_{31}$FN$_4$O$_3$S requires: 486, found: 487 (M+H$^+$, 100%).

Example 3

2,2,2-Trifluoro-N-[1-(3-{3-[(4-fluorophenylamino)methyl]-1-methyl-1H-pyrazol-5-yl}phenyl)-1-methylethyl]ethanesulfonamide

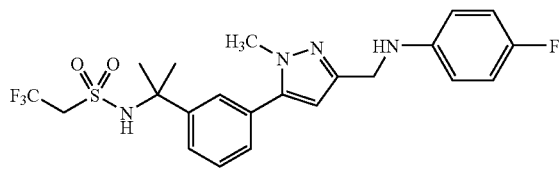

NaBH$_4$ (39 mg, 1.0 mmol) was added portionwise to a stirred mixture of the aldehyde from Example 1 Step 4 (100 mg, 0.26 mmol), 4-fluoroaniline (29 mg, 0.26 mmol), NaOAc (63 mg, 0.78 mmol), Na$_2$SO$_4$ (40 mg, 0.28 mmol), AcOH (0.22 mL) and EtOH (1.0 mL) at 0° C. The cooling bath was removed and the reaction allowed to warm to RT and stirred overnight. The solvent was then removed under reduced pressure and the mixture was taken up in CH$_2$Cl$_2$ (50 mL) and washed with NaHCO$_3$ solution (20 mL). The organic layer was concentrated under reduced pressure whilst dry loading on to MgSO$_4$ and then purified by column chromatography on silica eluting with 80% EtOAc/iso-hexane to yield the desired amine (89 mg, 72%). $^1$H NMR (CDCl$_3$, 360 MHz) δ 7.60-7.53 (2H, m), 7.47 (1H, t, J=7.6 Hz), 7.35 (1H, d, J=7.6 Hz), 6.90 (2H, app. t, J=8.7 Hz), 6.67-6.60 (2H, m), 6.26 (1H, s), 5.14 (1H, s), 4.30 (2H, s), 4.13-4.03 (1H, broad s), 3.86 (3H, s), 3.52-3.40 (2H, m), 1.80 (6H, s). MS (ES$^+$) C$_{22}$H$_{24}$F$_4$N$_4$O$_2$S requires: 484, found: 485 (M+H$^+$, 100%).

Example 4

2,2,2-Trifluoro-N-[1-(3-{3-[(ethyl{4-fluorophenyl}amino)methyl]-1-methyl-1H-pyrazol-5-yl}phenyl)-1-methylethyl]ethanesulfonamide

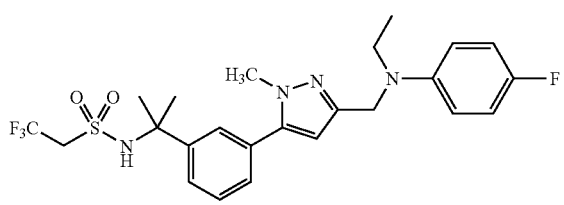

NaB(CN)H$_3$ (16 mg, 0.25 mmol) was added to a stirred solution of 2,2,2-trifluoro-N-[1-(3-{3-[(4-fluorophenylamino)methyl]-1-methyl-1H-pyrazol-5-yl}phenyl)-1-methylethyl]ethanesulfonamide (Example 3) (61 mg, 0.13 mmol) and acetaldehyde (11 mg, 0.25 mmol) in MeCN (5 mL), and AcOH (1 drop) and the mixture was stirred at RT for 16 hours. The mixture was concentrated under reduced pressure and then partitioned between NaHCO$_3$ solution (20 mL) and EtOAc (70 mL). The organics were washed with brine (20 mL) and concentrated under reduced pressure whilst dry loading onto MgSO$_4$. This residue was then purified by column chromatography on silica eluting with 100% Et$_2$O and then by normal phase preparative HPLC to yield the desired product (7.6 mg, 12%). $^1$H NMR (CDCl$_3$, 500 MHz) δ 7.55-7.48 (2H, m), 7.45 (1H, t, J=7.6 Hz), 7.32 (1H, d, J=7.6 Hz), 6.91 (2H, t, J=9 Hz), 6.78-6.71 (2H, m), 6.13 (1H, s), 4.91 (1H, s), 4.44 (2H, s), 3.85 (3H, s), 3.50-3.39 (4H, m), 1.80 (6H, s), 1.18 (3H, t, J=7.1 Hz). MS (ES$^+$) C$_{24}$H$_{28}$F$_4$N$_4$O$_2$S requires: 512, found: 513 (M+H$^+$, 100%).

Example 5

2,2,2-Trifluoroethanesulfonic acid [1-(3-{3-[1-(4-fluorophenoxy)-ethyl]-1-ethyl-1H-pyrazol-5-yl}-phenyl)-1-methylethyl]-amide

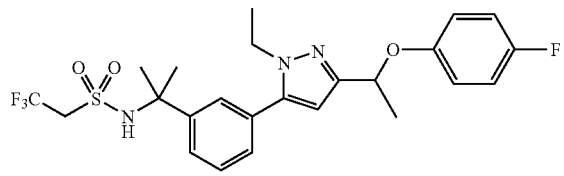

Step 1: 2,2,2-Trifluoroethanesulfonic acid {1-[3-(1-ethyl-3-formyl-1H-pyrazol-5-yl)-phenyl]-1-methylethyl}-amide

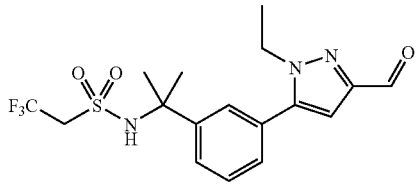

prepared by the procedure of Example 1 Steps 1-4, substituting ethylhydrazine for methylhydrazine in Step 1.

Step 2: 2,2,2-Trifluoroethanesulfonic acid (1-{3-[1-ethyl-3-(1-hydroxyethyl)-1H-pyrazol-5-yl]-phenyl}-1-methylethyl)-amide

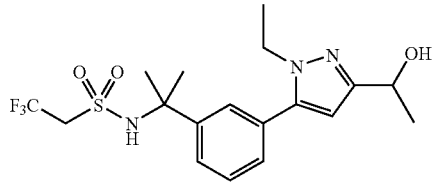

A solution of MeMgI (1.47 mmol) in Et$_2$O (3.0 M, 0.49 mL) was added dropwise over 2 min to a stirred mixture of the aldehyde from Step 1 and THF (10 mL) at 0° C. under N$_2$. The reaction mixture was stirred for 15 min and then quenched by the addition of NH$_4$Cl solution (15 mL). The organics were extracted into EtOAc (40 mL), concentrated under reduced pressure, and purified by column chromatography on silica, eluting with 80% EtOAc/iso-hexane to yield the alcohol (121 mg, 58%). $^1$H NMR (CDCl$_3$, 400 MHz) δ 7.60-7.45 (3H, m), 7.35 (1H, d, J=7.6 Hz), 6.23 (1H, s), 5.08 (1H, s), 4.98 (1H, q, J=6.5 Hz), 4.15-4.07 (2H, m), 3.53-3.42 (2H, m), 1.82 (6H, s), 1.57 (3H, d, J=6.5 Hz), 1.39 (3H, t, J=7.2 Hz). MS (ES$^+$) C$_{18}$H$_{24}$F$_3$N$_3$O$_3$S requires: 419, found: 420 (M+H$^+$, 100%).

Step 3: 2,2,2-Trifluoroethanesulfonic acid [1-(3-{3-[1-(4-fluorophenoxy)-ethyl]-1-ethyl-1H-pyrazol-5-yl}-phenyl)-1-methylethyl]-amide prepared following the procedure of Example 1 step 6 using the alcohol from Step 2 (121 mg, 0.29 mmol), 4-fluorophenol (49 mg, 0.44 mmol), PPh$_3$ (113 mg, 0.44 mmol), and DIAD (85 mg, 0.44 mmol). The crude mixture was purified by column chromatography on silica eluting with 70% Et$_2$O/iso-hexane and then by normal phase preparative HPLC to yield the ether (2.0 mg, 1%). $^1$H NMR (CDCl$_3$, 500 MHz) δ 7.60-7.45 (3H, m), 7.36-7.30 (1H, m), 7.00-6.90 (4H, m), 6.28 (1H, s), 5.40 (1H, q, J=6.6 Hz), 4.90 (1H, s), 3.53-3.42 (4H, m), 1.82 (6H, s), 1.69 (3H, d, J=6.5 Hz), 1.40 (3H, t, J=7.2 Hz). MS (ES$^+$) C$_{24}$H$_{27}$F$_4$N$_3$O$_3$S requires: 513, found: 514 (M+H$^+$, 100%).

Example 6

N-[1-(3-{1-Ethyl-3-[2-(4-fluorophenyl)ethyl]-1H-pyrazol-5-yl}phenyl)-1-methylethyl]-N'-(2,2,2-trifluoroethyl)sulfamide

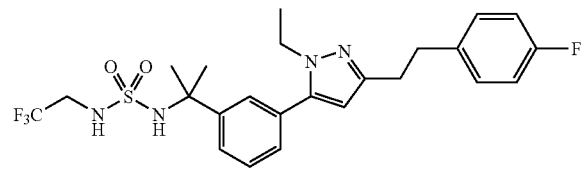

Step 1: 3-[5-(4-Fluorophenyl)-3-oxo-pentanoyl]-benzonitrile

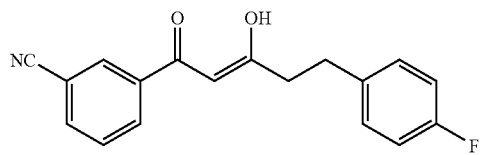

A solution of BuLi (119 mmol) in hexanes (1.6 M, 74.3 mL) was added dropwise over 15 min to a stirred solution of $^i$Pr$_2$NH (16.6 mL, 119 mmol) in THF (150 mL) at 0° C. under N$_2$. After 20 min, the reaction was cooled to −78° C. and a solution of 3-cyanoacetophenone (17.2 mL, 119 mmol) in THF (50 mL) was added dropwise over 5 min and then the mixture was stirred for a further hour.

Meanwhile, CDI (9.64 g, 59.4 mmol) was added to a stirred solution of 3-(4-fluorophenyl)propionic acid (10.0 g, 59.4 mmol) in THF (100 mL) at RT under N$_2$. This was then stirred at RT for 45 min and added by cannula into the above solution at −78° C. under N$_2$. The resulting solution was stirred at −78° C. for 45 min, before warming to RT and stirring for a further hour. The mixture was diluted with EtOAc (200 mL) and washed with 1M citric acid solution (2×100 mL), NaHCO$_3$ solution (2×100 mL) and brine (50 mL), dried (MgSO$_4$) and concentrated under reduced pressure. The residue was purified by column chromatography on silica eluting with 25% EtOAc/iso-hexane to yield the dicarbonyl compound (4.75 g, 27%). $^1$H NMR (CDCl$_3$, 360 MHz) δ 8.12 (1H, s), 8.05 (1H, d, J=8.0 Hz), 7.78 (1H, d, J=8.0 Hz), 7.57 (1H, t, J=8.0 Hz), 7.20-7.10 (2H, m), 7.04-6.92 (2H, m), 6.10 (1H, s), 3.00 (2H, t, J=8.6 Hz), 2.76 (2H, t, J=8.6 Hz).

Step 2: 3-{1-Ethyl-3-[2-(4-fluorophenyl)-ethyl]-1H-pyrazol-5-yl}-benzonitrile

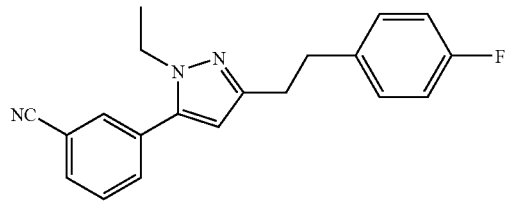

A mixture of 3-[5-(4-fluorophenyl)-3-oxo-pentanoyl]-benzonitrile (1.0 g, 3.39 mmol), ethyl hydrazine oxalate (763 mg, 5.08 mmol) and Et$_3$N (709 □L, 5.08 mmol) in EtOH (50 mL) was heated at reflux for 3 hours. The solvent was removed under reduced pressure and the residue was partitioned between EtOAc (100 mL) and H$_2$O (50 mL). The organics were separated, washed with brine (50 mL), concentrated under reduced pressure, and the residue purified by column chromatography on silica eluting with 40% EtOAc/iso-hexanes to yield first 3-{1-ethyl-5-[2-(4-fluorophenyl)-ethyl]-1H-pyrazol-3-yl}-benzonitrile (280 mg, 26%) (by-product) and then 3-{1-ethyl-3-[2-(4-fluorophenyl)-ethyl]-1H-pyrazol-5-yl}-benzonitrile (380 mg, 35%).

3-{1-Ethyl-5-[2-(4-fluorophenyl)-ethyl]-1H-pyrazol-3-yl}-benzonitrile (byproduct): $^1$H NMR (CDCl$_3$, 500 MHz) δ 8.06 (1H, s), 7.98 (1H, d, J=7.9 Hz), 7.58-7.42 (2H, m), 7.16-7.08 (2H, m), 7.04-6.93 (2H, m), 6.34 (1H, s), 4.03 (2H, q, J=7.3 Hz), 2.98 (2H, t, J=7.4 Hz), 2.91 (2H, t, J=7.4 Hz), 1.41 (3H, t, J=7.3 Hz). MS (ES$^+$) C$_{20}$H$_{18}$FN$_3$ requires: 319, found: 320 (M+H$^+$, 100%).

3-{1-Ethyl-3-[2-(4-fluorophenyl)-ethyl]-1H-pyrazol-5-yl}-benzonitrile: $^1$H NMR (CDCl$_3$, 500 MHz) δ 7.75-7.66 (2H, m), 7.63-7.55 (2H, m), 7.18 (2H, dd, J=8.5, 5.6 Hz), 6.96 (2H, t, J=8.5 Hz), 6.06 (1H, s), 4.09 (2H, q, J=7.3 Hz), 2.98-2.88 (4H, m), 1.39 (3H, t, J=7.3 Hz). MS (ES$^+$) C$_{20}$H$_{18}$FN$_3$ requires: 319, found: 320 (M+H$^+$, 100%).

Step 3: 1-(3-{1-Ethyl-3-[2-(4-fluorophenyl)-ethyl]-1H-pyrazol-5-yl}-phenyl)-1-methylethyl amine

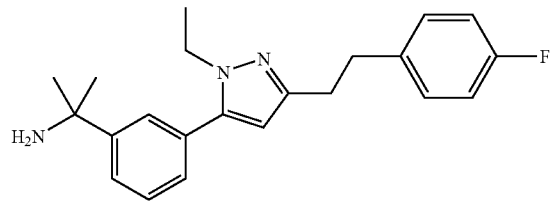

Prepared following the procedure of Example 1 Step 2, using the above 3-{1-ethyl-3-[2-(4-fluorophenyl)-ethyl]-1H-pyrazol-5-yl}-benzonitrile (380 mg, 1.19 mmol), CeCl$_3$ (1.76 g, 7.15 mmol) and MeLi (1.6 M in Et$_2$O, 4.45 mL, 7.15 mmol) to yield, after purification by column chromatography on deactivated alumina using 1-5% MeOH/CH$_2$Cl$_2$, the amine (133 mg, 32%). $^1$H NMR (CDCl$_3$, 360 MHz) δ

7.58-7.50 (2H, m), 7.40 (1H, t, J=7.7 Hz), 7.25 (3H, m), 6.97 (2H, t, J=8.7 Hz), 6.04 (1H, s), 4.10 (2H, q, J=7.2 Hz), 3.00-2.87 (4H, m), 1.52 (6H, s), 1.37 (3H, t, J=7.2 Hz).

Step 4: N-[1-(3-{1-Ethyl-3-[2-(4-fluorophenyl) ethyl]-1H-pyrazol-5-yl}phenyl)-1-methyl ethyl]-N'-(2,2,2-trifluoroethyl)sulfamide Prepared by the procedure of Example 1 Step 3. The amine from Step 3 (67 mg, 0.19 mmol), Et$_3$N (80 μL, 0.57 mmol) and 2,2,2-trifluoroethylsulfamoyl chloride (75 mg, 0.38 mmol) were reacted to yield after purification by column chromatography on silica using 80% Et$_2$O/iso-hexanes the title sulfamide (25 mg, 26%). $^1$H NMR (CDCl$_3$, 500 MHz) δ 7.57-7.49 (2H, m), 7.45 (1H, t, J=7.8 Hz), 7.30 (1H, d, J=7.8 Hz), 7.19 (2H, dd, J=8.7, 5.6 Hz), 6.97 (2H, t J=8.7 Hz), 6.03 (1H, s), 4.69 (1H, s), 4.39 (1H, t, J=5.4 Hz), 4.10 (2H, q, J=7.2 Hz), 3.57 (2H, quintet, J=5.4 Hz), 3.03-2.90 (4H, m), 1.78 (6H, s), 1.39 (3H, t, J=7.2 Hz). MS (ES$^+$) C$_{24}$H$_{28}$F$_4$N$_4$O$_2$S requires: 512, found: 513 (M+H$^+$, 100%).

Example 7

N-[1-(3-{1-Ethyl-5-[2-(4-fluorophenyl)ethyl]-1H-pyrazol-3-yl}phenyl)-1-methylethyl]-N'-(2,2,2-trifluoroethyl)sulfamide

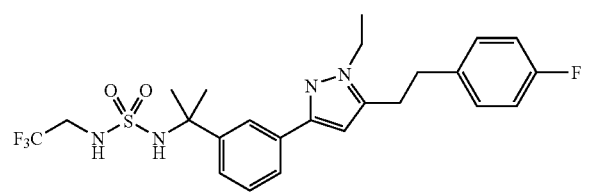

Prepared from the by-product of Example 6 Step 2, following the procedures of Example 6 Steps 3 and 4. Purified by column chromatography on silica using 70% Et$_2$O/iso-hexanes. $^1$H NMR (CDCl$_3$, 500 MHz) δ 7.97 (1H, s), 7.67-7.63 (1H, m), 7.44-7.38 (2H, m), 7.14 (2H, dd, J=8.4, 5.5 Hz), 6.99 (2H, t, J=8.5 Hz), 6.33 (1H, s), 4.70 (1H, s), 4.28 (1H, t, J=7.1 Hz), 4.02 (2H, q, J=7.2 Hz), 3.52 (2H, quintet, J=7.1 Hz), 2.99 (2H, t, J=7.7 Hz), 2.92 (2H, t, J=7.7 Hz), 1.80 (6H, s), 1.39 (3H, t, J=7.2 Hz). MS (ES$^+$) C$_{24}$H$_{28}$F$_4$N$_4$O$_2$S requires: 512, found: 513 (M+H$^+$, 100%).

Example 8

N-[1-(3-{3-[2-(4-Fluorophenyl)ethyl]-1,4-dimethyl-1H-pyrazol-5-yl}phenyl)-1-methylethyl]-N'-(2,2,2-trifluoroethyl)sulfamide

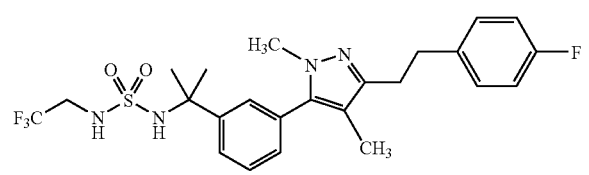

Step 1: 3-[5-(4-Fluorophenyl)-2-methyl-3-oxo-pentanoyl]-benzonitrile

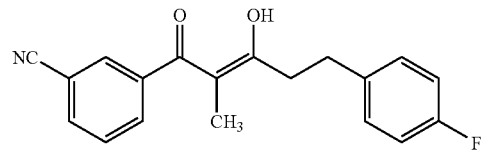

A mixture of 3-[5-(4-fluorophenyl)-3-oxo-pentanoyl]-benzonitrile (Example 6 Step 1) (1.0 g, 3.39 mmol), K$_2$CO$_3$ (469 mg, 3.39 mmol), MeI (264 μL, 4.23 mmol) and acetone (25 mL) was heated at 60° C. for 36 hours and then concentrated under reduced pressure. The residue was partitioned between H$_2$O (20 mL) and Et$_2$O (80 mL) and acidified to pH=3 using 2 M HCl solution. The organics were separated and concentrated under reduced pressure. The residue was purified by column chromatography on silica using 30% EtOAc/iso-hexanes to yield the alkylated product (0.63 g, 60%). $^1$H NMR (CDCl$_3$, 360 MHz) δ 8.14 (1H, s), 8.04 (1H, d, J=8.0 Hz), 7.83 (1H, d, J=7.7 Hz), 7.57 (1H, J=7.8 Hz), 7.08-7.00 (2H, m), 6.87 (2H, t, J=8.6 Hz), 4.38 (1H, q, J=7.0 Hz), 2.85-2.70 (4H, m), 1.43 (3H, d, J=7.0 Hz). MS (ES$^-$) C$_{19}$H$_{16}$FNO$_2$ requires: 309, found: 308 (M+H$^+$, 100%).

Step 2: 3-{3-[2-(4-Fluorophenyl)ethyl]-1,4-dimethyl-1H-pyrazol-5-yl}-benzonitrile

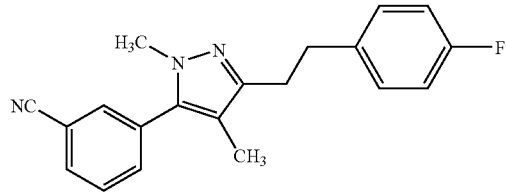

EtOH (20 mL) and methyl hydrazine (162 μL, 3.05 mmol) were added to the product of Step 1 (630 mg, 2.04 mmol) and the mixture heated at reflux for 90 min. The solvent was removed under reduced pressure and the residue purified by column chromatography on silica eluting with 40% EtOAc/iso-hexanes to yield first 3-{5-[2-(4-fluorophenyl)-ethyl]-1,4-dimethyl-1H-pyrazol-3-yl}-benzonitrile (213 mg, 33%) (byproduct) and then the desired 3-{3-[2-(4-fluorophenyl)-ethyl]-1,4-dimethyl-1H-pyrazol-5-yl}-benzonitrile (250 mg, 38%).

3-{5-[2-(4-Fluorophenyl)-ethyl]-1,4-dimethyl-1H-pyrazol-3-yl}-benzonitrile: $^1$HNMR (CDCl$_3$, 500 MHz) δ 7.94 (1H, s), 7.88 (1H, d, J=7.8 Hz), 7.57 (1H, d, J=7.8 Hz), 7.49 (1H, t, J=7.8 Hz), 7.02 (2H, dd, J=8.5, 5.7 Hz), 6.97 (2H, t, J=8.5 Hz), 3.64 (3H, s), 2.89 (2H, t, J=6.7 Hz), 2.83 (2H, t, J=6.7 Hz), 2.01 (3H, s).

3-{3-[2-(4-Fluorophenyl)-ethyl]-1,4-dimethyl-1H-pyrazol-5-yl}-benzonitrile: $^1$H NMR (CDCl$_3$, 500 MHz) δ 7.71 (1H, d, J=7.7 Hz), 7.63-7.55 (2H, m), 7.53 (1H, d, J=7.7 Hz), 7.18 (2H, dd, J=8.5, 5.5 Hz), 6.98 (2H, t, J=8.5 Hz), 3.73 (3H, s), 2.97-2.92 (2H, m), 2.88-2.82 (2H, m), 1.84 (3H, s).

Step 3: 1-(3-{3-[2-(4-Fluorophenyl)ethyl]-1,4-dimethyl-1H-pyrazol-5-yl}-phenyl)-1-methylethyl amine

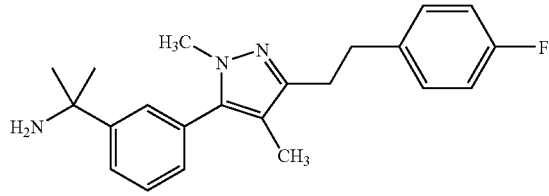

Prepared by the procedure of Example 1 Step 2 using 3-{3-[2-(4-fluorophenyl)-ethyl]-1,4-dimethyl-1H-pyrazol-5-yl}-benzonitrile (250 mg, 0.81 mmol), CeCl$_3$ (1.2 g, 4.9 mmol) and MeLi (1.6 M in Et$_2$O, 3.05 mL, 4.9 mmol) to yield, after purification by column chromatography on deactivated alumina using 2-5% MeOH/CH$_2$Cl$_2$, the title amine (72 mg, 26%). $^1$H NMR (CDCl$_3$, 500 MHz) δ 7.56 (1H, d, J=8.0 Hz), 7.45-7.36 (2H, m), 7.20-7.13 (3H, m), 6.97 (2H, t, J=8.6 Hz), 3.74 (3H, s), 3.03-2.95 (2H, m), 2.90-2.85 (2H, m), 1.87 (3H, s), 1.53 (6H, s). MS (ES$^+$) C$_{22}$H$_{26}$FN$_3$ requires: 351, found: 352 (M+H$^+$, 30%).

Step 4: N-[1-(3-{3-[2-(4-Fluorophenyl)ethyl]-1,4-dimethyl-1H-pyrazol-5-yl}phenyl)-1-methylethyl]-N'-(2,2,2-trifluoroethyl)sulfamide Prepared by the procedure of Example 1 Step 3 using the amine from Step 3 (72 mg, 0.20 mmol), Et$_3$N (114 μL, 0.82 mmol) and 2,2,2-trifluoroethylsulfamoyl chloride (121 mg, 0.61 mmol) to yield, after purification by column chromatography on silica using 80-100% Et$_2$O/iso-hexanes the title sulfamide (23 mg, 22%). $^1$H NMR (CDCl$_3$, 500 MHz) δ 7.54 (1H, d, J=7.8 Hz), 7.48 (1H, t, J=7.8 Hz), 7.42 (1H, s), 7.23 (1H, d, J=7.5 Hz), 7.19 (2H, dd, J=8.5, 5.6 Hz), 6.97 (2H, t, J=8.5 Hz), 4.71 (1H, s), 4.43 (1H, t, J=7.4 Hz), 3.74 (3H, s), 3.57 (2H, quintet, J=7.4 Hz), 2.98-2.92 (2H, m), 2.87-2.82 (2H, m), 1.87 (3H, s), 1.79 (6H, s). MS (ES$^+$) C$_{24}$H$_{28}$F$_4$N$_4$O$_2$S requires: 512, found: 513 (M+H$^+$, 100%).

Examples 9-15

The following were prepared by the procedure of Example 6, using the appropriate hydrazine in the second step and the appropriate sulfamoyl chloride in the final step:

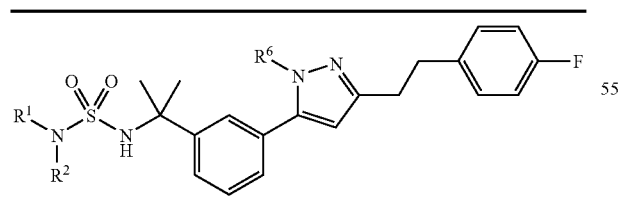

| Example | R$^1$ | R$^2$ | R$^6$ | MS (ES$^+$) (M + H$^+$) |
|---|---|---|---|---|
| 9 | 2,2,2-trifluoroethyl | H | n-propyl | 527 |
| 10 | 2,2,2-trifluoroethyl | H | isopropyl | 527 |
| 11 | cyclobutyl | H | methyl | 471 |
| 12 | cyclopropylmethyl | H | methyl | 471 |
| 13 | n-propyl | H | methyl | 459 |

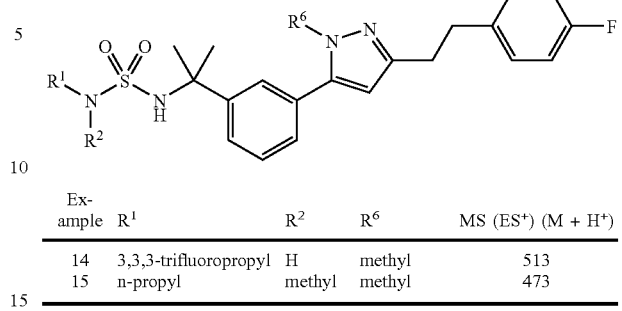

| Example | R$^1$ | R$^2$ | R$^6$ | MS (ES$^+$) (M + H$^+$) |
|---|---|---|---|---|
| 14 | 3,3,3-trifluoropropyl | H | methyl | 513 |
| 15 | n-propyl | methyl | methyl | 473 |

Example 16

N-[1-(3-{5-[2-(4-Fluorophenyl)ethyl]-1-methyl-1H-pyrazol-3-yl}phenyl)ethyl]-N'-(2,2,2-trifluoroethyl)sulfamide

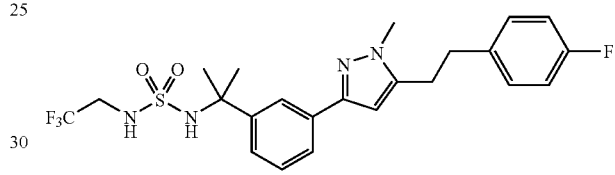

Step 1: 3-{5-[2-(4-Fluorophenyl)-ethyl]-1-methyl-1H-pyrazol-3-yl}-benzonitrile

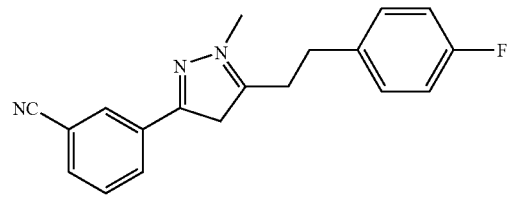

Prepared by the procedures of Example 6 Steps 1 and 2, using methylhydrazine in the second step and retaining the 1-methyl-1H-pyrazol-3-yl isomer.

Step 2: N-[1-(3-{5-[2-(4-Fluorophenyl)ethyl]-1-methyl-1H-pyrazol-3-yl}phenyl)ethyl]-N'-(2,2,2-trifluoroethyl)sulfamide A solution of the nitrile from Step 1 (50 mg, 0.16 mmol) in THF (5 mL) was treated with MeMgI in Et$_2$O (3.0 M, 0.32 mL, 0.96 mmol). A milky solution formed, which was stirred at RT for 30 mins, then further MeMgI was added (1.0 mL, 3 mmol) and stirred for 1 hour. A solution of LiAlH$_4$ in THF (1.0 M, 2.5 mL, 2.5 mmol) was added and stirred at RT for 1 hour. The reaction was quenched by addition of H$_2$O and the solvent evaporated under reduced pressure. The residue was partitioned between CH$_2$Cl$_2$ and H$_2$O, the CH$_2$Cl$_2$ layer was separated and the aqueous layer re-extracted with CH$_2$Cl$_2$. The combined organic extracts were washed with brine, dried (MgSO$_4$) and concentrated to give crude 1-(3-

{5-[2-(4-fluorophenyl)-ethyl]-1-methyl-1H-pyrazol-3-yl}-phenyl)-ethylamine as a yellow gum (50 mg).

This amine was dissolved in CH$_2$Cl$_2$ (5 mL) and treated with 2,2,2-trifluoroethylsulfamoyl chloride (91 mg, 0.45 mmol) and Et$_3$N (63 μL, 0.45 mmol) and stirred at RT for 30 min. The solvent was evaporated under reduced pressure and the residue purified by silica chromatography eluting with 2% MeOH/CH$_2$Cl$_2$ to yield the title sulfamide as a colourless gum (18 mg, 23% over 2 steps). $^1$H NMR (CDCl$_3$, 500 MHz) δ 7.80-7.76 (1H, s), 7.65 (1H, d, J=7.8 Hz), 7.38 (1H, t, J=7.8 Hz), 7.23 (1H, d, J=7.8 Hz), 7.18-7.10 (2H, m), 6.98 (2H, t, J=8.7 Hz), 6.35 (1H, s), 4.66-4.56 (2H, m), 4.38-4.28 (1H, m), 3.69 (3H, s), 3.53-3.42 (1H, m), 3.42-3.30 (1H, m), 3.02-2.84 (4H, m), 1.62-1.52 (3H, m). MS (ES$^+$) C$_{22}$H$_{24}$F$_4$N$_4$O$_2$S requires: 484, found: 485 (M+H$^+$).

Example 17

N-Cyclobutyl-N'-(1-{3-[3-(4-fluorobenzyl)-1-methyl-1H-pyrazol-5-yl]phenyl}-1-methylethyl)sulfamide

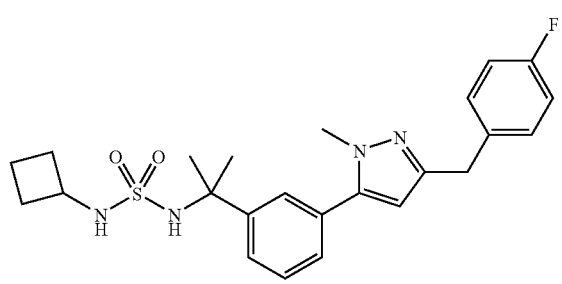

Step 1: 3-(4-Fluorobenzyl)-5-(3-iodophenyl)-1-methyl-1H-pyrazole

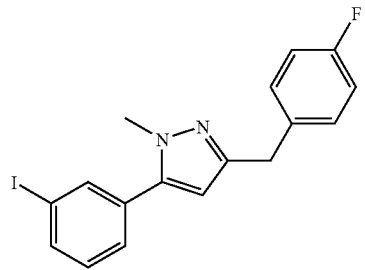

A solution of $^i$Pr$_2$NH (11.2 mL, 80 mmol) in THF (100 mL) was cooled in an ice/salt bath and $^n$BuLi (80 mmol) in hexanes (1.6M, 50 mL) was added dropwise. The solution was stirred for 1 h, then cooled to −78° C. A solution of 3-iodoacetophenone (19.7 g, 80 mmol) in THF (30 mL) was added dropwise and stirred for 1 h at −78° C., then a solution of methyl 4-fluorophenylacetate (13.4 g, 80 mmol) in THF (30 mL) was added. The mixture was stirred for 24 h while warming to RT. Acetic acid (9 mL) and EtOH (100 mL) were added, followed by MeNHNH$_2$ (4.2 mL, 80 mmol). The mixture was heated to 60° C. for 1 h and, after cooling, the solvent was removed under reduced pressure. The residue was partitioned between CH$_2$Cl$_2$ and H$_2$O, the CH$_2$Cl$_2$ layer was separated and retained and the aqueous layer re-extracted with CH$_2$Cl$_2$. The combined organic extracts were washed with brine, dried (MgSO$_4$), and evaporated. The residue was purified by silica chromatography eluting with 50-80% CH$_2$Cl$_2$/iso-hexane to yield 3-(4-fluorobenzyl)-5-(3-iodophenyl)-1-methyl-1H-pyrazole, as the second of two pyrazole isomers, as a brown oil (4.5 g, 15%). $^1$H NMR (CDCl$_3$, 500 MHz) δ 7.72 (1H, s), 7.69 (1H, d, J=8.0 Hz), 7.31 (1H, d, J=8.0 Hz), 7.26-7.20 (2H, m), 7.13 (1H, t, J=8.0 Hz), 6.96 (2H, t, J=8.8 Hz), 6.01 (1H, s), 3.93 (2H, s), 3.81 (3H, s). MS (ES$^+$) C$_{17}$H$_{14}$FIN$_2$ requires: 392, found: 393 (M+H$^+$).

Step 2: 3-[3-(4-Fluorobenzyl)-1-methyl-1H-pyrazol-5-yl]-benzonitrile

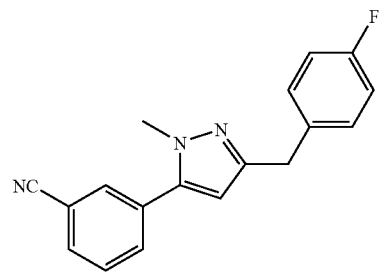

A solution of the iodophenyl derivative from Step 1 (2 g, 5.1 mmol) in NMP (10 mL) was treated with zinc cyanide (418 mg, 3.5 mmol) and Pd(PPh$_3$)$_4$ (400 mg, 0.35 mmol) and heated at 170° C. in a preheated oil bath for 30 min. Further Pd(PPh$_3$)$_4$ (400 mg, 0.35 mmol) was added and heating continued for a further 30 min. The cooled reaction mixture was diluted with CH$_2$Cl$_2$ and loaded onto a silica column which was eluted with 100% CH$_2$Cl$_2$. The product was collected, concentrated and further purified in the same way to yield 3-[3-(4-fluorobenzyl)-1-methyl-1H-pyrazol-5-yl]-benzonitrile as a yellow oil (600 mg, 41%).

$^1$H NMR (CDCl$_3$, 360 MHz) δ 7.70-7.58 (3H, m), 7.55 (1H, t, J=8.0 Hz), 7.29-7.20 (2H, m), 6.98 (2H, t, J=8.7 Hz), 6.07 (1H, s), 3.96 (2H, s), 3.85 (3H, s). MS (ES$^+$) C$_{18}$H$_{14}$FN$_3$ requires 291: found: 292 (M+H$^+$).

Step 3: N-Cyclobutyl-N'-(1-{3-[3-(4-fluorobenzyl)-1-methyl-1H-pyrazol-5-yl]phenyl}-1-methylethyl)sulfamide Crushed CeCl$_3$ (630 mg, 2.6 mmol) was dried under vacuum at 170° C. for 1 h, then cooled and the flask filled with N$_2$. THF (20 mL) was added and the resultant milky solution cooled to −78° C. A solution of MeLi in Et$_2$O (1.6 M, 1.6 mL, 2.6 mmol) was added and the temperature maintained at −78° C. for 1 h. A solution of 3-[3-(4-fluorobenzyl)-1-methyl-1H-pyrazol-5-yl)-benzonitrile in THF (10 mL) was added and after 5 min the cooling bath was removed and the reaction stirred overnight gradually warming to RT. The reaction was quenched by the addition of MeOH, and the solvents evaporated under reduced pressure. The residue was triturated with CH$_2$Cl$_2$, then filtered and the solid washed well with CH$_2$Cl$_2$. The combined organics were washed with NaHCO$_3$ solution, then brine, dried (MgSO$_4$) and evaporated under reduced pressure to give crude 1-{3-[3-(4-fluorobenzyl)-1-methyl-1H-pyrazol-5-yl]-phenyl}-1-methylethylamine as a yellow gum (70 mg).

The crude amine was dissolved in CH$_2$Cl$_2$ (5 mL) and Et$_3$N (222 μL, 1.6 mmol) and crude cyclobutylsulfamoyl chloride (136 mg, ca. 0.8 mmol) were added and the reaction was stirred at RT for 30 min. The reaction was evaporated under reduced pressure and diluted with MeCN:DMSO (1:1, 2 mL) and filtered. The filtrate was injected on to a reverse phase HPLC system and the title compound was isolated, after basic workup, as a yellow gum (4 mg, 1% over 2 steps). $^1$H NMR (CDCl$_3$, 500 MHz) δ 7.52-7.48 (2H, m), 7.41 (1H, t, J=8.6 Hz), 7.31-7.23 (3H, m), 6.98 (2H, t, J=8.8 Hz), 6.02 (1H, s), 4.49 (1H, s), 4.10 (1H, d, J=8.4 Hz), 3.96 (2H, s), 3.85 (3H, s), 3.82-3.73 (1H, m), 2.30-2.21 (2H, m), 1.90-1.79 (2H, m), 1.73 (6H, s), 1.72-1.63 (2H, m). MS (ES$^+$) C$_{24}$H$_{29}$FN$_4$O$_2$S requires 456: found: 457 (M+H$^+$).

Example 18

N-(1-{3-[5-(4-Fluorophenyl)-1-methyl-1H-pyrazol-3-yl]phenyl}-1-methylethyl)-N'-(2,2,2-trifluoroethyl)sulfamide

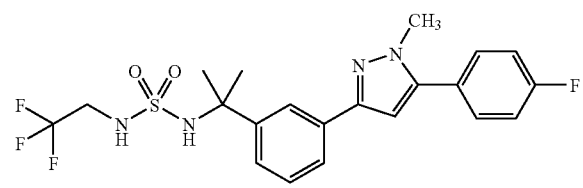

Step 1: 5-(4-Fluorophenyl)-1-methyl-1,2-dihydro-pyrazol-3-one and 5-(4-Fluorophenyl)-2-methyl-1,2-dihydro-pyrazol-3-one

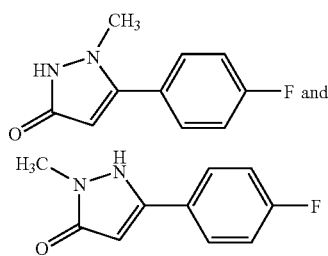

A suspension of (4-fluorophenyl)propynoic acid methyl ester (1.6 g, 9.0 mmol) in MeOH (10 mL) and H$_2$O (10 mL) was heated at 60° C. and MeNHNH$_2$ (0.5 mL, 9.4 mmol) was added. The reaction mixture was stirred at 60° C. for 20 min. then filtered. The residue was washed with H$_2$O (10 mL) and MeOH (5 mL) and dried to give 5-(4-fluorophenyl)-1-methyl-1,2-dihydro-pyrazol-3-one (0.63 g, 36%). The filtrate was then concentrated under reduced pressure and the residue dissolved in EtOAc (20 ml) and washed with H$_2$O (3×15 mL). The aqueous layer was acidified to pH 5.5 with 2 M citric acid solution (3×15 mL) and extracted with EtOAc (3×20 mL). The extracts were dried (MgSO$_4$) and concentrated under reduced pressure to give 5-(4-fluorophenyl)-2-methyl-1,2-dihydro-pyrazol-3-one (0.2 g, 12%).

5-(4-Fluorophenyl)-1-methyl-1,2-dihydro-pyrazol-3-one: $^1$H NMR (d$_6$-DMSO, 360 MHz) δ 11.01 (1H, s), 7.69-7.73 (2H, m), 7.16 (2H, t, J=8.9 Hz), 5.77 (1H, s), 3.55 (3H, s). MS (ES$^+$) C$_{10}$H$_9$FN$_2$O requires: 192, found: 193 (M+H$^+$, 100%).

5-(4-Fluorophenyl)-2-methyl-1,2-dihydro-pyrazol-3-one: $^1$H NMR (d$_6$-DMSO, 360 MHz) δ 9.65 (1H, s), 7.54-7.50 (2H, m), 7.30 (2H, t, J=8.9 Hz), 5.61 (1H, s), 3.60 (3H, s). MS (ES$^+$) C$_{10}$H$_9$FN$_2$O requires: 192, found: 193 (M+H$^+$, 100%).

Step 2: Trifluoromethanesulfonic acid 5-(4-fluorophenyl)-1-methyl-1H-pyrazol-3-yl ester

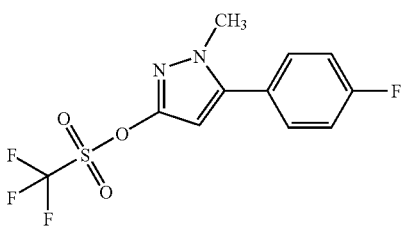

A suspension of 5-(4-fluorophenyl)-1-methyl-1,2-dihydro-pyrazol-3-one (0.63 g, 3.3. mmol) in dry pyridine (6 ml) was cooled to −10° C. and triflic anhydride (0.58 mL, 3.4 mmol) was added. The reaction mixture was gradually warmed to RT and stirred for 2 hours, then poured into 2 N HCl (20 mL) and extracted with EtOAc (3×20 mL). The combined organic layers were washed with 2 N HCl (ca. 40 mL), until washings were pH 1, and then washed with brine (15 mL) and saturated NaHCO$_3$ solution (15 mL), dried (MgSO$_4$) and evaporated under reduced pressure. The residue was purified by column chromatography on silica eluting with 35% CH$_2$Cl$_2$/iso-hexane to give the triflate (0.91 g, 86%). $^1$H NMR (CDCl$_3$, 360 MHz) δ 7.41-7.38 (2H, m), 7.18 (2H, t, J=8.5 Hz), 6.16 (1H, s), 3.80 (3H, s). MS (ES$^+$) C$_{11}$H$_8$F$_4$N$_2$O$_3$S requires: 324, found: 325 (M+H$^+$, 100%).

Step 3: 3-[5-(4-Fluoro-phenyl)-1-methyl-1H-pyrazol-3-yl]-benzonitrile

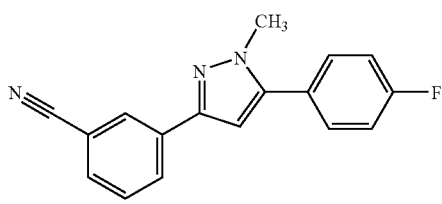

3-Cyanophenylboronic acid (60 mg, 0.4 mmol) and 2M Na$_2$CO$_3$ solution (0.4 mL, 0.8 mmol) were added to a solution of the triflate from Step 2 (0.2 g, 0.6 mmol) in toluene (5 mL). The reaction mixture was degassed with a flow of N$_2$ for 5 min and then Pd(PPh$_3$)$_4$ (50 mg, 0.06 mmol) was added. The mixture was heated at reflux for 8 hours and cooled to RT. 4N NaOH solution (20 mL) and EtOAc (30 mL) were added, and the organic layer separated, dried (MgSO$_4$), and concentrated under reduced pressure. The residue was purified by column chromatography on silica eluting with 20% EtOAc/iso-hexane to give the title compound (53 mg, 48%). $^1$H NMR (CDCl$_3$, 360 MHz) δ 8.11 (1H, s), 8.03 (1H, d, J=7.8 Hz), 7.58 (1H, d, J=7.8 Hz), 7.50 (1H, t, J=7.8 Hz), 7.46-7.42 (2H, m), 7.19 (2H, t, J=8.4 Hz), 6.60 (1H, s), 3.91 (3H, s). MS (ES$^+$) C$_{17}$H$_{12}$FN$_3$ requires: 277, found: 278 (M+H$^+$ 100%).

Step 4: 1-{3-[5-(4-Fluorophenyl)-1-methyl-1H-pyrazol-3-yl]-phenyl}-1-methylethyl amine

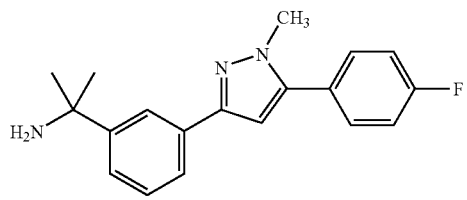

Prepared by the procedure of Example 1 Step 2 using the nitrile from Step 3 (100 mg, 0.4 mmol), CeCl$_3$ (0.7 g, 2.9 mmol) and MeLi (1.6 M in Et$_2$O, 1.8 mL, 2.9 mmol) to yield, after purification by column chromatography on deactivated alumina using 2% MeOH/CH$_2$Cl$_2$, the amine (50 mg, 45%). MS (ES$^+$) C$_{19}$H$_{20}$FN$_3$ requires: 309, found: 310 (M+H$^+$).

Step 5: N-(1-{3-[5-(4-Fluorophenyl)-1-methyl-1H-pyrazol-3-yl]phenyl}-1-methylethyl)-N'-(2,2,2-trifluoroethyl)sulfamide

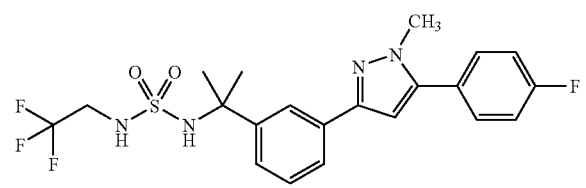

2,2,2-Trifluoroethylsulfamoyl chloride (53 mg, 0.3 mmol) was added dropwise to a stirred solution of the amine from Step 4 (50 mg, 0.2 mmol) and Et$_3$N (37 µL, 0.3 mmol) in CH$_2$Cl$_2$ (2 m]L) at RT under N$_2$. The mixture was stirred at RT overnight and then diluted with CH$_2$Cl$_2$ (25 mL), washed with NaHCO$_3$ solution (20 m L), dried (MgSO$_4$) and concentrated under reduced pressure. The crude product was purified by column chromatography on silica eluting with 20% EtOAc/iso-hexane to yield the title sulfamide (5 mg, 6%). $^1$H NMR (CDCl$_3$, 500 MHz) δ 8.02 (1H, s), 7.69 (1H, d, J=6.6 Hz), 7.45-7.42 (4H, m), 7.18 (2H, t, J=8.6 Hz), 6.58 (1H, s), 4.70 (1H, s), 4.30-4.27 (1H, m), 3.90 (3H, s), 3.57-3.53 (2H, m), 1.80 (6H, s). MS (ES$^+$) C$_{21}$H$_{22}$F$_4$N$_4$O$_2$S requires: 470, found: 471 (M+H$^+$, 100%).

Example 19

N-(1-{3-[3-(4-Fluorophenyl)-1-methyl-1H-pyrazol-5-yl]phenyl}-1-methylethyl)-N'-(2,2,2-trifluoroethyl)sulfamide

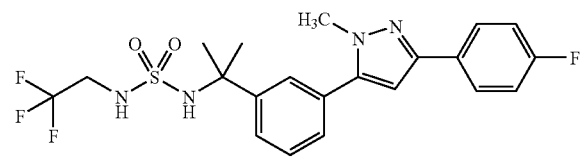

Prepared by the procedure of Example 18, using the isomeric 5-(4-fluorophenyl)-2-methyl-1,2-dihydro-pyrazol-3-one in Step 2.

The crude product was purified by column chromatography on silica eluting with 30% EtOAc/iso-hexane to yield the title sulfamide. $^1$H NMR (CDCl$_3$, 500 MHz) δ 7.80-7.77 (2H, m), 7.59-7.55 (2H, m), 7.49 (1H, t, J=7.6 Hz), 7.40 (1H, d, J=7.6 Hz), 7.10 (2H, t, J=8.7 Hz), 6.56 (1H, s), 4.73 (1H, s), 4.46-4.43 (1H, m), 3.92 (3H, s), 3.61-3.58 (2H, m), 1.80 (6H, s). MS (ES$^+$) C$_{21}$H$_{22}$F$_4$N$_4$O$_2$S requires: 470, found: 471 (M+H$^+$, 100%).

Example 20

N-{1-[3-(1-Ethyl-3-{[4-(trifluoromethyl)-3,6-dihydropyridin-1(2H)-yl]methyl}-1H-pyrazol-5-yl)phenyl]-1-methylethyl}-2,2,2-trifluoroethanesulfonamide

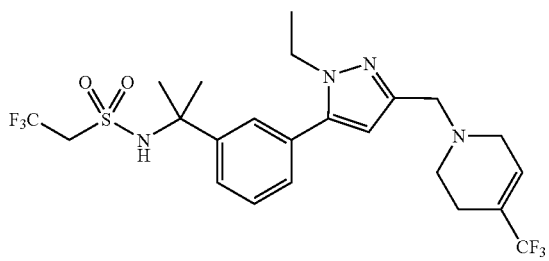

Step 1: N-(1-{3-[3-(Chloromethyl)-1-ethyl-1H-pyrazol-5-yl]-phenyl}-1-methylethyl)-2,2,2-trifluoroethanesulfonamide

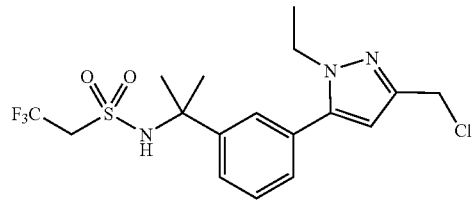

The procedure of Example 1 steps 1-5 was repeated using ethyl hydrazine in step 1. The resulting alcohol (0.136 mg, 0.33 mmol) in dichloromethane (5 ml) was treated with thionyl chloride (0.073 ml, 1 mmol) at room temperature and stirred for 2 hours. The organic phase was washed with water (10 ml) and brine (10 ml), dried over MgSO$_4$, filtered and evaporated, to give 0.13 g. MS (ES$^+$) 423 (M+H$^+$, 100%).

Step 2: N-{1-[3-(1-Ethyl-3-{[4-(trifluoromethyl)-3,6-dihydropyridin-1(2H)-yl]methyl}-1H-pyrazol-5-yl)phenyl]-1-methylethyl}-2,2,2-trifluoroethanesulfonamide

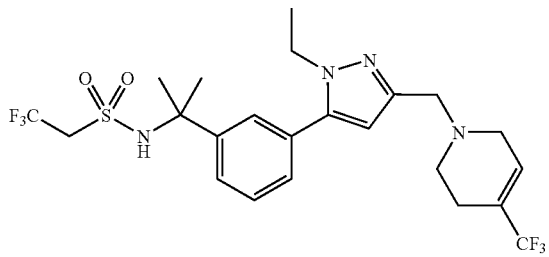

The chloride from Step 1 (45 mg, 0.106 mmol) was dissolved in dimethylformamide (3 ml) and treated with triethylamine (0.03 ml, 0.212 mmol) and the appropriate amine (20 mg, 0.108 mmol). The reaction was then heated to 80° C. for 16 hours. The reaction was then diluted with water (20 ml) and the products extracted into ethyl acetate (2×20 ml). The combined organic phase was washed with brine, dried over MgSO₄ and evaporated to dryness. The product was isolated using silica gel chromatography eluting with hexane-ethyl acetate mixtures to give 0.06 g. ¹H NMR (CDCl₃, 360 MHz) δ 7.57-7.54 (2H, m), 7.48 (1h, t, J=7.6 Hz), 7.35 (1H, d, J=7.5 Hz), 6.26 (1H, s), 6.29 (1H, m), 5.01 (1H, brs), 4.15-4.11 (2H, q, J=7.1, 14 Hz), 3.70 (2H, s), 3.49-3.43 (2H, q, J=8.7, 17.6 Hz), 3.20 (2H, m), 2.74 (2H, t, J=5.6 Hz), 2.32 (2H, m), 1.82 (6H, s) and 1.39 (3H, t, J=7.2 Hz). MS (ES⁺) 539 (M+H⁺, 100%).

Example 21

N-[1-3-{3-[(4,4-Difluoropiperidin-1-yl)methyl]-1-ethyl-1H-pyrazol-5-yl}phenyl)-1-methylethyl]-2,2,2-trifluoroethanesulfonamide

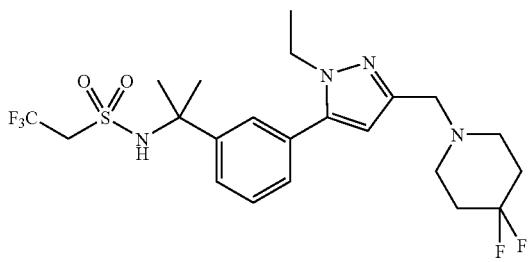

Following the procedure as outlined in Example 20 using 4,4-difluoropiperidine as amine; 0.04 g isolated. ¹H NMR (CDCl₃, 360 MHz) δ 7.56-7.54 (2H, m), 7.48 (1H, m), 7.35 (1H, d, J=7.5 Hz), 6.22 (1H, s), 5.02 (1H, brs), 4.15-4.11 (2H, q, J=7.1, 14 Hz), 3.62 (2H, s), 3.48-3.43 (2H, q, J=8.7, 17.5 Hz), 2.64-2.62 (4H, m), 2.06-1.97 (4H, m), 1.82 (6H, s) and 1.38 (3H, t, J=7.1 Hz). MS (ES⁺) 509 (M+H⁺, 100%).

Example 22

N-{1-[3-(1-Ethyl-3-{[(3,3,3-trifluoropropyl)amino]methyl}-1H-pyrazol-5-yl)phenyl]-1-methylethyl}-2,2,2-trifluoroethanesulfonamide

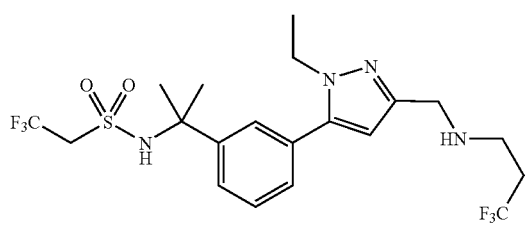

Following the procedure as outlined in Example 20 using 3,3,3-trifluoropropylamine as amine; 0.04 g isolated. ¹H NMR (CDCl₃, 360 MHz) δ 7.51-7.46 (3H, m), 7.36-7.33 (1H, m), 6.21 (1H, s), 4.91 (1H, brs), 4.13-4.09 (2H, q, J=6.5, 13 Hz), 3.85 (2H, s), 3.48-3.44 (2H, q, J=7.8, 15.8 Hz), 2.97 (2H, t, J=6.5 Hz), 2.40-2.32 (2H, m), 1.82 (6H, s), 1.65 (1H, brs) and 1.40 (3H, t, J=6.4 Hz). MS (ES⁺) 501(M+H⁺).

Example 23

N-{1-[3-(1-Ethyl-5-{[4-(trifluoromethyl)piperidin-1-yl]methyl}-1H-pyrazol-3-yl)phenyl]-1-methylethyl}-2,2,2-trifluoroethanesulfonamide

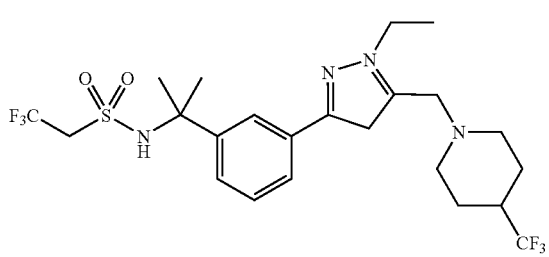

Steps 1-4 of Example 1 were repeated, using ethyl hydrazine in place of methyl hydrazine, and using 3-(5-dimethoxymethyl-1-ethyl-1H-pyrazol-3-yl)-benzonitrile from the first step.

The resulting aldehyde (50 mg, 0.13 mmol) in 1,2-dichloroethane (5 ml) was treated with 4-trifluoromethylpiperidine (21 mg, 0.14 mmol), triethylamine (35 μl, 0.26 mmol) and sodium triacetoxyborohydride (40 mg, 0.20 mmol). The mixture was stirred for 4 h and diluted with dichloromethane, washed with saturated aqueous sodium hydrogencarbonate, water, brine, dried (MgSO₄), filtered and evaporated. The crude product was purified by flash chromatography (2:1 iso-hexane/ethyl acetate) to give a white foam (45 mg). ¹H NMR (ppm) (CDCl₃) δ 1.38 (3 H, t, J=7.2 Hz), 1.82 (6H, s), 2.55 (4H, s), 3.39-3.49 (2 H, q, J=8.2 Hz), 3.58 (2 H, s), 3.74 (4H, t, J=4.6 Hz), 4.15 (2 H, q, J=7.1 Hz), 5.30 (1 H, br s), 6.24 (1 H, s), 7.35 (1 H, d, J=7.7 Hz), 7.48 (1 H, t, J=7.7 Hz), 7.55 (2 H, m). MS(MH⁺) 475.

Example 24

N-(1-{3-[1-Ethyl-3-(morpholin-4-ylmethyl)-1H-pyrazol-5-yl]phenyl}-1-methylethyl)-2,2,2-trifluoroethanesulfonamide

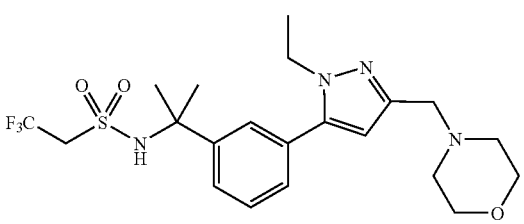

Prepared as in Example 23, using the aldehyde obtained as in Example 1 (steps 1-4), using ethyl hydrazine in Step 1 and taking forward the isomer 3-(3-dimethoxymethyl-1-ethyl-1H-pyrazol-5-yl)-benzonitrile. The final step, following the method of Example 23, was carried out using morpholine as amine. ¹H NMR (ppm) (CDCl₃) δ 1.38 (3 H, t, J=7.2 Hz), 1.82 (6 H, s), 2.55 (4 H, s), 3.39-3.49 (2 H, q, J=8.2 Hz), 3.58 (2 H, s), 3.74 (4 H, t, J=4.6 Hz), 4.15 (2 H, q, J=7.1 Hz), 5.30 (1 H, br), 6.24 (1 H, s), 7.35 (1 H, d, J=7.7 Hz), 7.48 (1 H, t, J=7.7 Hz), 7.55 (2 H, m). MS(MH⁺) 475.

Examples 25-35

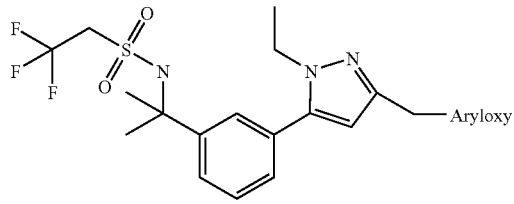

Prepared by the procedure described in Example 1 (using ethyl hydrazine in place of methyl hydrazine in step 1) using the appropriate phenols in Step 6.

| Example no | Aryloxy | Formula | MW | m/z (ES+) (M + 1) |
|---|---|---|---|---|
| 25 | ⌬–O– | $C_{23}H_{26}F_3N_3O_3S$ | 481 | 482 |
| 26 | 2-F-C6H4-O– | $C_{23}H_{25}F_4N_3O_3S$ | 499 | 500 |
| 27 | 4-CN-C6H4-O– | $C_{24}H_{25}F_3N_4O_3S$ | 506 | 507 |
| 28 | 3-OMe-C6H4-O– | $C_{24}H_{28}F_3N_3O_4S$ | 511 | 512 |
| 29 | 3-F-C6H4-O– | $C_{23}H_{25}F_4N_3O_3S$ | 499 | 500 |
| 30 | 4-Cl-C6H4-O– | $C_{23}H_{25}ClF_3N_3O_3S$ | 515, 517 | 516, 518 |
| 31 | 2-Cl-C6H4-O– | $C_{23}H_{25}ClF_3N_3O_3S$ | 515, 517 | 516, 518 |
| 32 | 3-CN-C6H4-O– | $C_{24}H_{25}F_3N_4O_3S$ | 506 | 507 |
| 33 | 2-CN-C6H4-O– | $C_{24}H_{25}F_3N_4O_3S$ | 506 | 507 |
| 34 | 2-Br-4-F-C6H3-O– | $C_{23}H_{25}BrF_4N_3O_3S$ | 578 | 578, 580 |
| 35 | 2-CN-4-F-C6H3-O– | $C_{24}H_{25}F_4N_4O_3S$ | 524 | 525 |

Examples 36-46

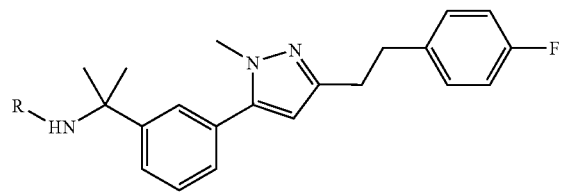

Prepared by the procedure of Example 6, using methyl hydrazine in Step 2, and the appropriate sulfamoyl or sulfonyl chloride in Step 4.

| Example no | R | Formula | MW | M/z (ES+) (M + 1) |
|---|---|---|---|---|
| 36 | CF3CH2NHSO2Me | $C_{23}H_{26}F_4N_4O_2S$ | 498 | 499 |
| 37 | CF3CH2SO2Me | $C_{23}H_{25}F_3N_3O_2S$ | 483 | 484 |
| 38 | PrNHSO2Me | $C_{24}H_{31}FN_4O_2S$ | 458 | 459 |
| 39 | 5-Cl-thiophene-2-SO2Me | $C_{24}H_{25}ClFN_3O_2S_2$ | 517, 519 | 518, 520 |

-continued

| Example no | R | Formula | MW | M/z (ES+) (M + 1) |
|---|---|---|---|---|
| 40 | (N-tert-butyl methanesulfonamide group) | $C_{25}H_{33}FN_4O_2S$ | 472 | 473 |
| 41 | (N-neopentyl methanesulfonamide group) | $C_{26}H_{35}FN_4O_2S$ | 486 | 487 |
| 42 | (N-cyclopentyl methanesulfonamide group) | $C_{26}H_{33}FN_4O_2S$ | 484 | 485 |
| 43 | (N-cyclobutyl methanesulfonamide group) | $C_{26}H_{33}FN_4O_2S$ | 484 | 485 |
| 44 | (N-butyl methanesulfonamide group) | $C_{25}H_{33}FN_4O_2S$ | 472 | 473 |
| 45 | (N-isopropyl methanesulfonamide group) | $C_{24}H_{31}FN_4O_2S$ | 458 | 459 |
| 46 | (N-ethyl methanesulfonamide group) | $C_{23}H_{29}FN_4O_2S$ | 444 | 445 |

Example 47

N-[1-(6-{1-Ethyl-3-[(4-fluorophenoxy)methyl]-1H-pyrazol-5-yl}pyridin-2-yl)-1-methylethyl]-2,2,2-trifluoroethanesulfonamide

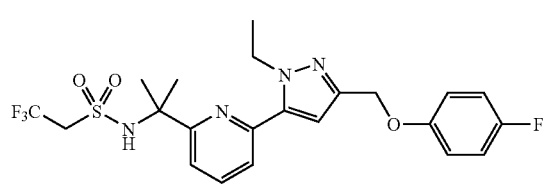

Step 1: 2-Bromo-6-(1H-imidazol-1-ylcarbonyl)pyridine

6-Bromopicolinic acid (4.015 g 19.8 mmol) was mixed with dichloromethane (16 ml), and carbonyl diimidazole (5.147 g, 31.7 mmole) was added to the suspension. After stirring overnight, the solution was washed with saturated sodium hydrogen carbonate solution (25 ml) and water (15 ml), dried over MgSO$_4$ and evaporated to a brown oil (3.91 g 78%). The resulting activated acid was used directly in the next step.

Step 2: 1-(6-Bromopyridin-2-yl)-4,4-dimethoxybutane-1,3-dione

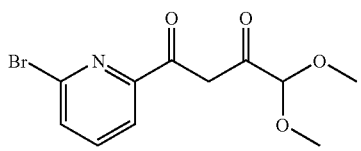

Diisopropylamine (4.6 ml, 30 mmol) in THF (25 ml) was cooled to 0° C., n-butyllithium (1.6 M in hexane, 20.6 ml, 33 mmol) was added, and the mixture cooled in dry ice/acetone with stirring for 1 hr. 1,1-Dimethoxy acetone (3.9 g, 33 mmol) in THF (20 ml) was added, and stirring continued for 1 hr. The activated acid (step 1) (3.9 g, 15 mmol) was suspended in THF (35 ml), added to the reaction, and stirring continued for 40 mins. After warming to room temperature, citric acid (1 M solution in water, 50 ml) was added and the product extracted with ether (2×50 ml). Drying over MgSO$_4$ and evaporation yielded 4.44 g product, used in the next step without further purification.

Step 3: 2-Bromo-6-[3-(dimethoxymethyl)-1-ethyl-1H-pyrazol-5-yl]pyridine

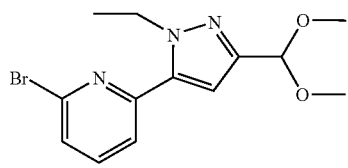

Prepared from the product of Step 2 using the procedure of Example 6 Step 2 to give the titled product, 2.75 g.

$^1$H NMR (CDCl$_3$, 360 MHz) 7.59 (1H, t, J=7.2 Hz), 7.53 (1H, d, J=7.2 Hz), 7.42 (1H, d, J=7.7 Hz), 6.65 (1H, s), 5.49 (1H, s), 4.67 (2H, q, J=7.1 Hz), 3.41 (6H, s), 1.45 (3H, t, J=7.1 Hz)

Step 4: 6-[3-(Dimethoxymethyl)-1-ethyl-1H-pyrazol-5-yl]pyridine-2-carbonitrile

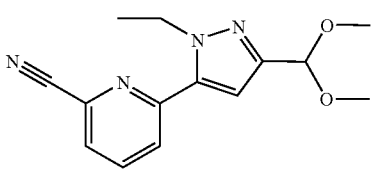

2-Bromo-6-[3-(dimethoxymethyl)-1-ethyl-1H-pyrazol-5-yl]pyridine from Step 3 (2.7 g, 8 mmol), Pd(PPh$_3$)$_4$ (0.36 g, 0.3 mmol) and zinc cyanide (544 mg, 4.6 mmol) in NMP (80 ml) were heated at 170° C. for 1 hr. After cooling to room temperature, water (30 ml) was added and the mixture extracted with ether (2×50 ml). The combined organic layers were washed with brine (30 ml), dried over MgSO$_4$ and evaporated.

Chromatography of the residue on silica gel eluting with 5:1 isohexane:ethyl acetate yielded desired product (1.50 g 66%).

$^1$H NMR (CDCl$_3$, 360 MHz) 7.89(1H, t, J=7.2 Hz), 7.80 (1H, d, J=7.2 Hz), 7.63 (1H, d, J=7.2 Hz), 6.73 (1H, s), 5.49 (1H, s), 4.69 (2H, q, J=7.1 Hz), 3.42 (6H, s), 1.25 (3H, t, J=7.1 Hz).

Step 5: N-[1-(6-{1-Ethyl-3-[(4-fluorophenoxy)methyl]-1H-pyrazol-5-yl}pyridin-2-yl)-1-methylethyl]-2,2,2-trifluoroethanesulfonamide

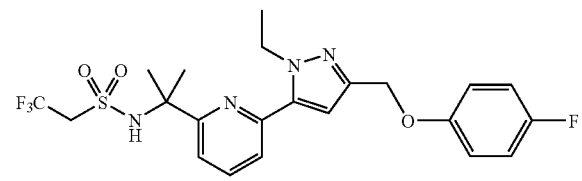

Prepared from the product of Step 4 by the procedure of Example 1 Steps 2-6.

$^1$H NMR (CDCl$_3$, 500 MHz) 7.83 (1H, t, J=7.9 Hz), 7.53 (1H, d, J=7.7 Hz), 7.41 (1H, d, J=7.8 Hz), 6.97 (4H, s), 6.66 (1H,s), 6.53 (1H,s), 5.08 (2H, s), 4.59 (2H, q, J=7.2 Hz), 3.79 (2H, q, J=8.8 Hz), 1.83 (6H, s), 1.51 (3H, t, J=7.2 Hz). MS (ES+) C$_{22}$H$_{24}$F$_4$N$_4$O$_3$S requires 500 found 501

Examples 48-50

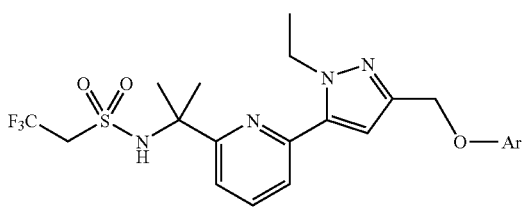

Using the procedure of Example 47 the following were prepared:

| Example | OAr | Formula | MW | m/z (ES+) (M + 1) |
|---|---|---|---|---|
| 48 | ![structure] | C$_{22}$H$_{23}$F$_5$N$_4$O$_3$S | 518 | 519 |
| 49 | ![structure] | C$_{22}$H$_{23}$F$_5$N$_4$O$_3$S | 518 | 519 |
| 50 | ![structure] | C$_{23}$H$_{24}$F$_3$N$_5$O$_3$S | 507 | 508 |

GLOSSARY

RT—room temperature
DIAD—diisopropylazodicarboxylate
CDI—1,1'-carbonyldiimidazole
TFA—trifluoroacetic acid
AcOH—acetic acid
NMP—N-methylpyrrolidone

The invention claimed is:
1. A compound of formula I:

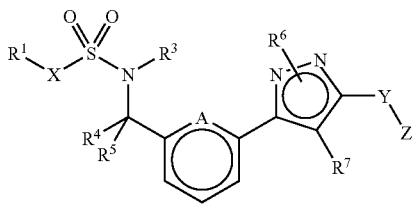

wherein:
A represents CH;
X represents a bond, O or NR$^2$;
Y represents a bond, (CHR$^8$)$_n$, CR$^8$=CR$^8$, O—CHR$^8$, CHR$^8$—O or CHR$^8$—NR$^8$, where n is 1 or 2 and each R$^8$ is independently H or C$_{1-4}$alkyl;
Z represents Ar or N(R$^9$)$_2$, with the proviso that when Z represents N(R$^9$)$_2$, Y represents a bond or (CHR$^8$)$_n$;
R$^1$ represents a hydrocarbon group selected from the group consisting of C$_{1-10}$alkyl, C$_{3-10}$cycloalkyl, C$_{3-6}$cycloalkyl C$_{1-6}$alkyl, C$_{2-10}$alkenyl and phenyl which is optionally substituted with up to 3 halogen atoms;
R$^2$ represents H or C$_{1-4}$alkyl;
R$^3$ represents H or C$_{1-4}$alkyl;
R$^4$ represents C$_{1-6}$alkyl,
R$^5$ represents H or C$_{1-6}$alkyl;
R$^6$ is bonded to one of the nitrogen atoms of the pyrazole ring and represents a hydrocarbon group of 1-5 carbon atoms selected from the group consisting of methyl, ethyl, n-propyl, isopropyl, n-butyl, sec-butyl, t-butyl, cyclopropyl, cyclopropylmethyl and allyl, which is optionally substituted with up to 3 halogen atoms;
R$^7$ represents H or C$_{1-6}$alkyl;
R$^9$ represents H or C$_{1-6}$ alkyl which is optionally substituted with up to 3 halogen atoms, provided that at least one R$^9$ is not H; and Ar represents phenyl which bears 0-3 substituents independently selected from halogen, $CF_3$, $CHF_2$, $CH_2F$, $NO_2$, CN, $OCF_3$, $C_{1-6}$alkyl and $C_{1-6}$alkoxy;

or a pharmaceutically acceptable salt thereof.

2. A compound according to claim 1 wherein X is a bond and $R^1$ represents $C_{1-6}$alkyl which is optionally substituted with up to 3 fluorine atoms, or phenyl or benzyl, either of which is optionally substituted with chlorine or fluorine.

3. A compound according to claim 2 wherein $R_1$ is selected from n-propyl, n-butyl, 2,2,2-trifluoroethyl, benzyl, or 4-fluorophenyl.

4. A compound according to claim 1 wherein X is O and $R^1$ represents alkyl, alkenyl, cycloalkyl or cycloalkylalkyl of up to 6 carbon atoms which is optionally substituted with up to 3 fluorine atoms.

5. A compound according to claim 1 wherein X is NH or NMe and $R^1$ represents alkyl, alkenyl, cycloalkyl or cycloalkylalkyl of up to 6 carbon atoms which is optionally substituted with up to 3 fluorine atoms.

6. A compound according to claim 5 wherein $R^1$ is selected from ethyl, n-propyl, isopropyl, n-butyl, 2,2-dimethylpropyl, t-butyl, 2,2,2-trifluoroethyl, 3,3,3-trifluoropropyl, cyclobutyl, cyclopentyl and cyclopropylmethyl.

7. A compound according to claim 1 wherein Z is Ar and Y is selected from $CH_2$, $OCH_2$, $CH_2CH_2$ and $CH_2O$.

8. A pharmaceutical composition comprising a compound according to claim 1 and a pharmaceutically acceptable carrier.

* * * * *